United States Patent
Rambin

(10) Patent No.: US 6,340,354 B1
(45) Date of Patent: *Jan. 22, 2002

(54) AUTOMATED COMPULSORY BLOOD EXTRACTION SYSTEM

(76) Inventor: Christopher L Rambin, 620 1/2 Durden Ave., Ruston, LA (US) 71270

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/858,097

(22) Filed: May 17, 1997

Related U.S. Application Data

(60) Provisional application No. 60/017,633, filed on May 17, 1996.

(51) Int. Cl.⁷ .............................................. A61B 17/20
(52) U.S. Cl. .................... 604/22; 604/319; 604/543; 600/583; 606/178
(58) Field of Search ................... 604/35, 147, 319, 604/540, 541, 19, 22, 543, 115; 606/167, 170, 171, 176–178, 82, 169; 600/573, 580, 583

(56) References Cited

U.S. PATENT DOCUMENTS 1,934,046 A * 11/1933 Demarchi .................... 604/115
2,696,212 A * 12/1954 Dunmire (List continued on next page.)

OTHER PUBLICATIONS

Smoot, Ruiz–Inchaustegul, and Roth, "Mechanical Leech Therapy to Relieve Venous Congestion", Journal of Reconstructive Microsurgery vol. 11 Jan. 95.

Hartrampf, Drazan, Noel, "A Mechanical Leech for Transverse Rectus Abdominis Musculocutaneous Flaps", Annals of Plastic Surgery vol. 31 #2 Aug. 93.

(List continued on next page.)

Primary Examiner—Anhtuan T. Nguyen
Assistant Examiner—Jeremy Thissell
(74) Attorney, Agent, or Firm—Joseph T Regard, Ltd

(57) ABSTRACT

A method and apparatus for the treatment of thrombosis, venous insufficiency, and the like, and in particular to an Automated Compulsory Blood Extraction System (ACBES) configured to provide an efficient and safe means for the measured extraction of blood utilizing a device providing, in effect, an artificial leech, but without the infection, control, care, and other limitations associated with the medicinal leech. The preferred embodiment of the present invention utilizes recent micro technological advances to provide a micro mechanical device which mimics and improves upon the bloodletting properties of the medicinal leech utilizing a micro mechanical valve, micropump, and micro sensor arraignment cooperating with a tertiary jaw array having teeth situated thereon. The preferred embodiment of the present invention contemplates an extraction device which may have a head size of one centimeter or less, and which may be utilized in number about the affected area of the patient to provide controlled, precision, pulsed blood extraction via vacuum induction, supplying a controlled dosage of anticoagulant, histamine anesthetic, or the like. Alternative embodiments of the present invention include an independent, single needle, stationary design configured primarily for emergency use, a multi-needle piston design, a large extraction area array design including concentric needles of adjustable depth, and a deep extraction needle design.

31 Claims, 41 Drawing Sheets

U.S. PATENT DOCUMENTS

| | | | | |
|---|---|---|---|---|
| 2,743,723 A | * | 5/1956 | Hein | 604/115 |
| 3,628,405 A | * | 12/1971 | Fleisher | 81/3.42 |
| 3,649,996 A | * | 3/1972 | Marti | |
| 4,299,219 A | * | 11/1981 | Norris, Jr. | 604/115 |
| 4,385,630 A | * | 5/1983 | Gilcher et al. | 604/31 |
| 4,447,237 A | * | 5/1984 | Frisch et al. | 604/175 |
| 4,545,374 A | * | 10/1985 | Jacobson | 606/61 |
| 4,617,700 A | * | 10/1986 | Batorfalvi et al. | 452/69 |
| 4,662,376 A | * | 5/1987 | Belanger | 604/115 |
| 4,671,790 A | * | 6/1987 | Nishi | 604/131 |
| 4,765,332 A | * | 8/1988 | Fischell et al. | 606/159 |
| 5,192,294 A | * | 3/1993 | Blake, III | 606/184 |
| 5,282,788 A | * | 2/1994 | Wilk et al. | |
| 5,632,717 A | * | 5/1997 | Yoon | |
| 5,776,092 A | * | 7/1998 | Farin et al. | |

OTHER PUBLICATIONS

Baker, Nayduch, "Medicinal Leech Therapy: a Case Study", Orthopaedic Nursing, Mar./Apr. 1989, vol. 8, No. 2.

* cited by examiner

Top View

Side View

Bottom View

End View

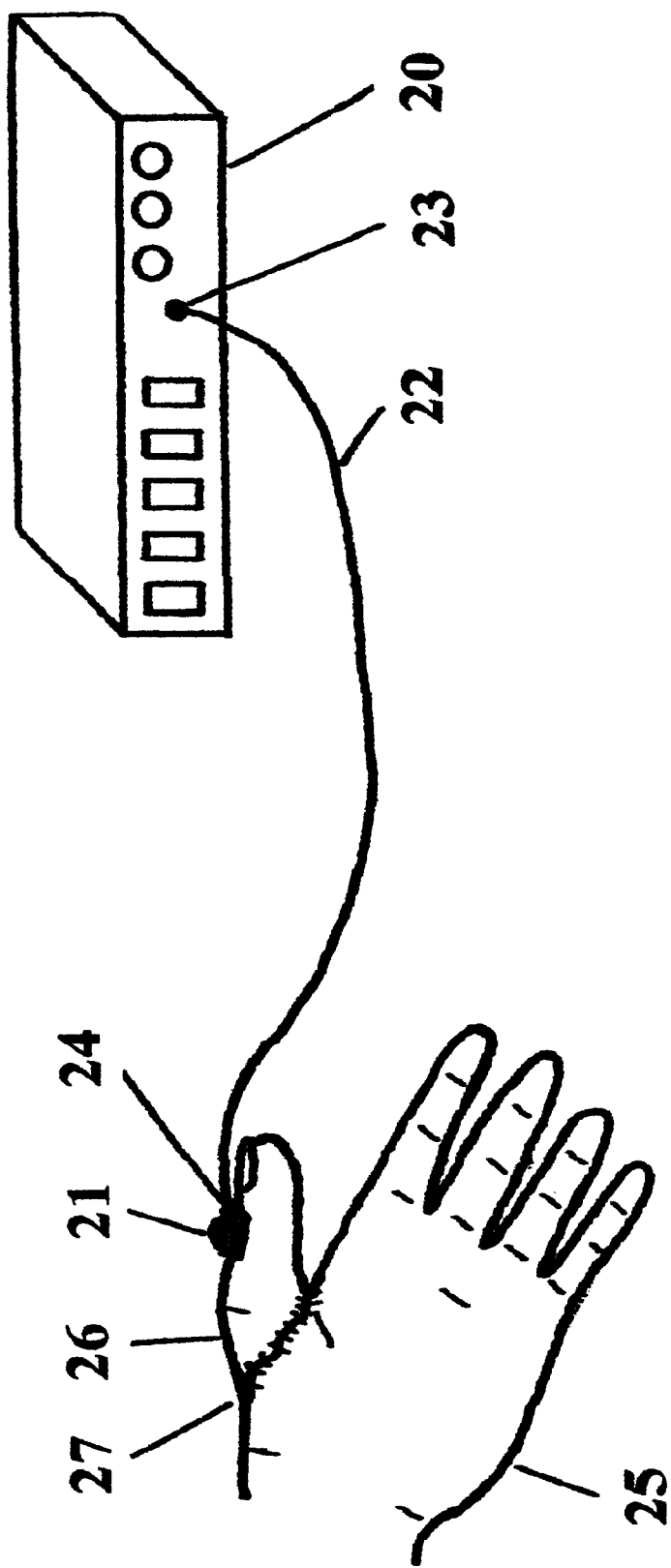

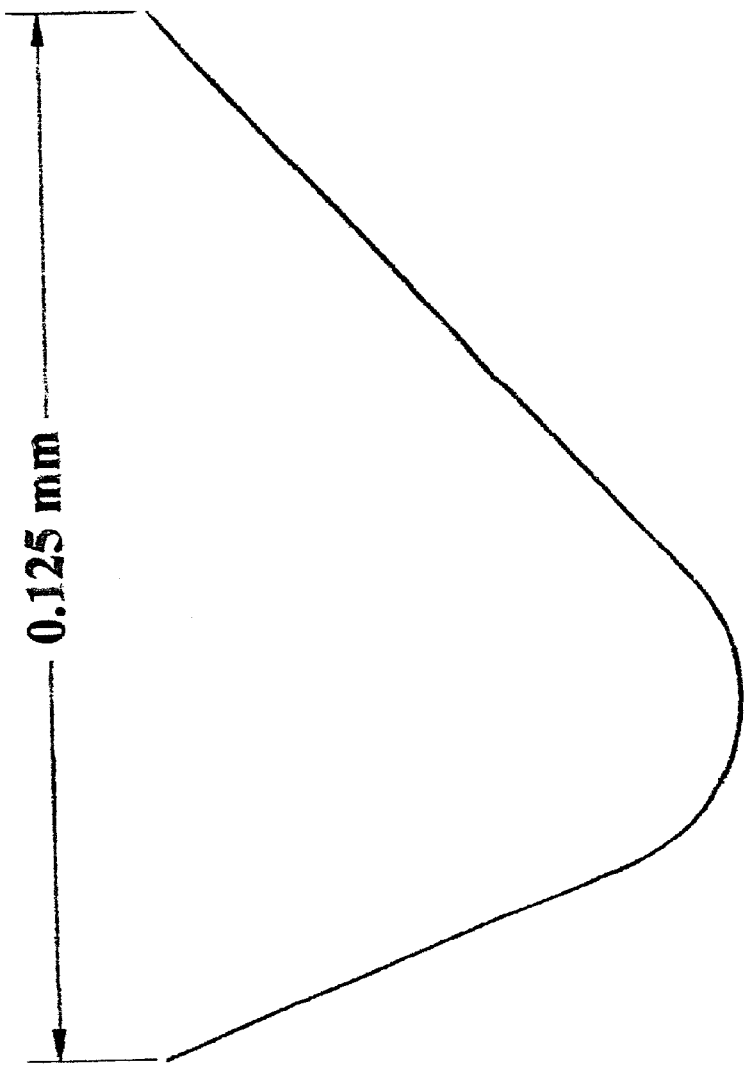

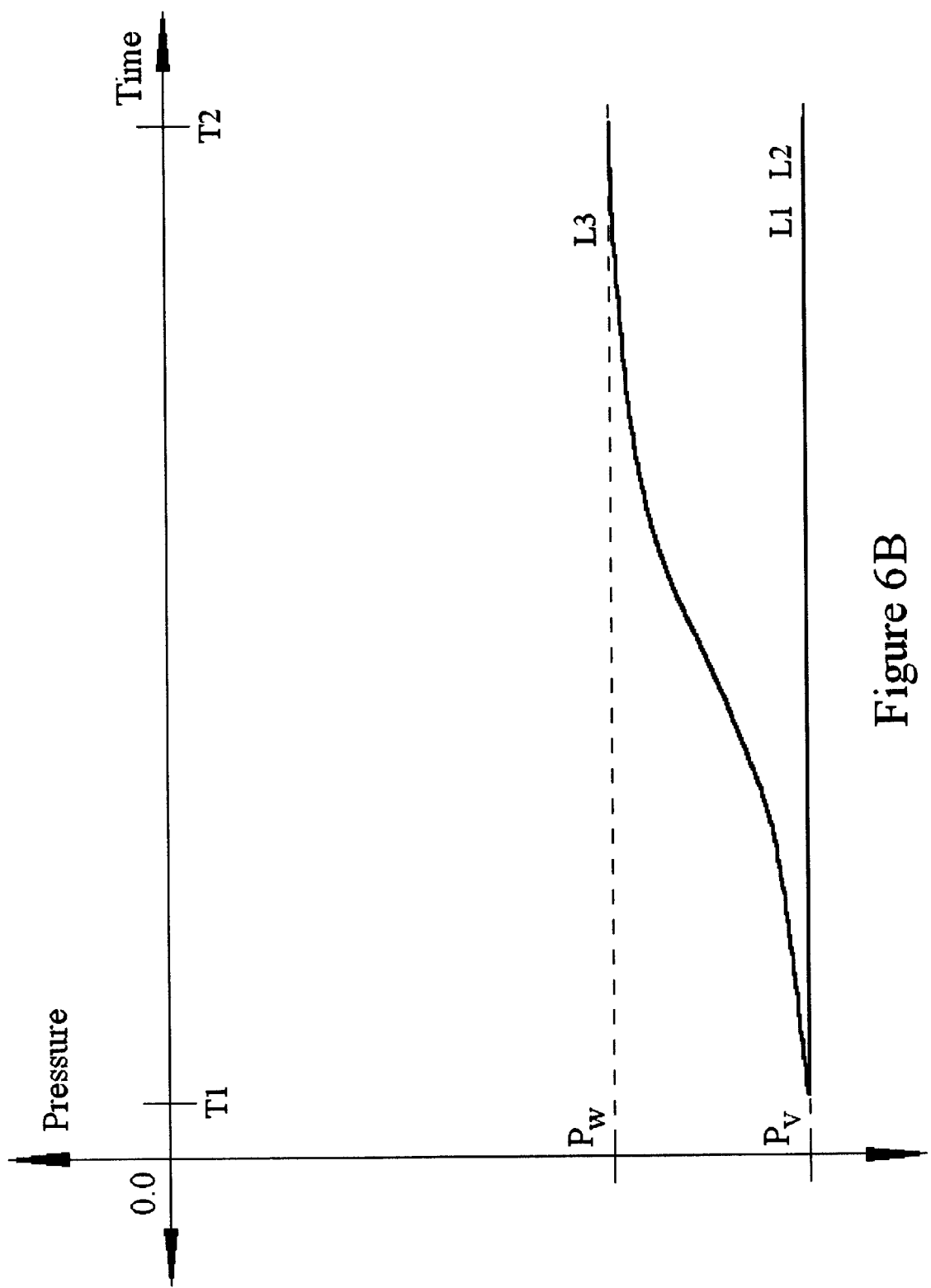

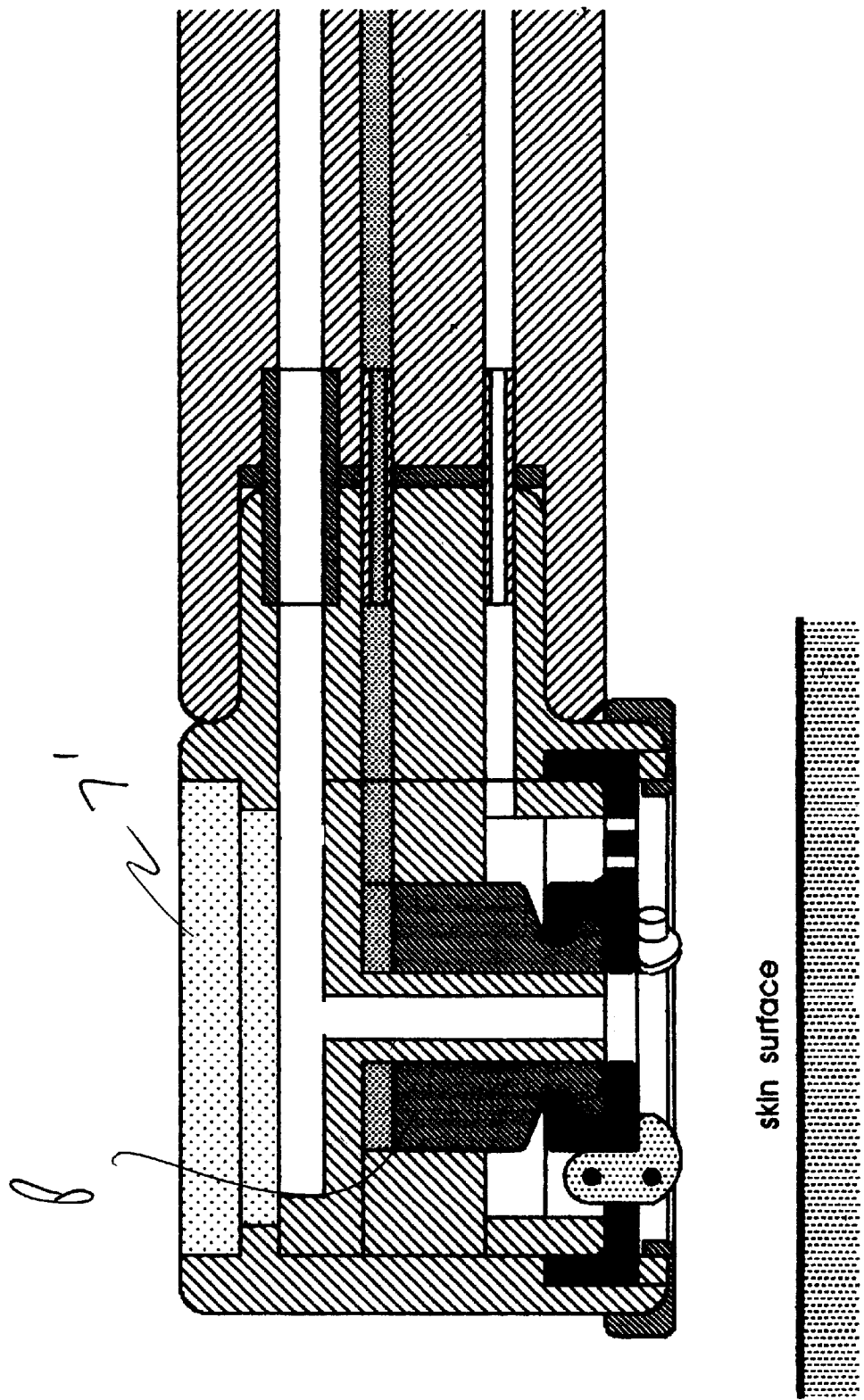

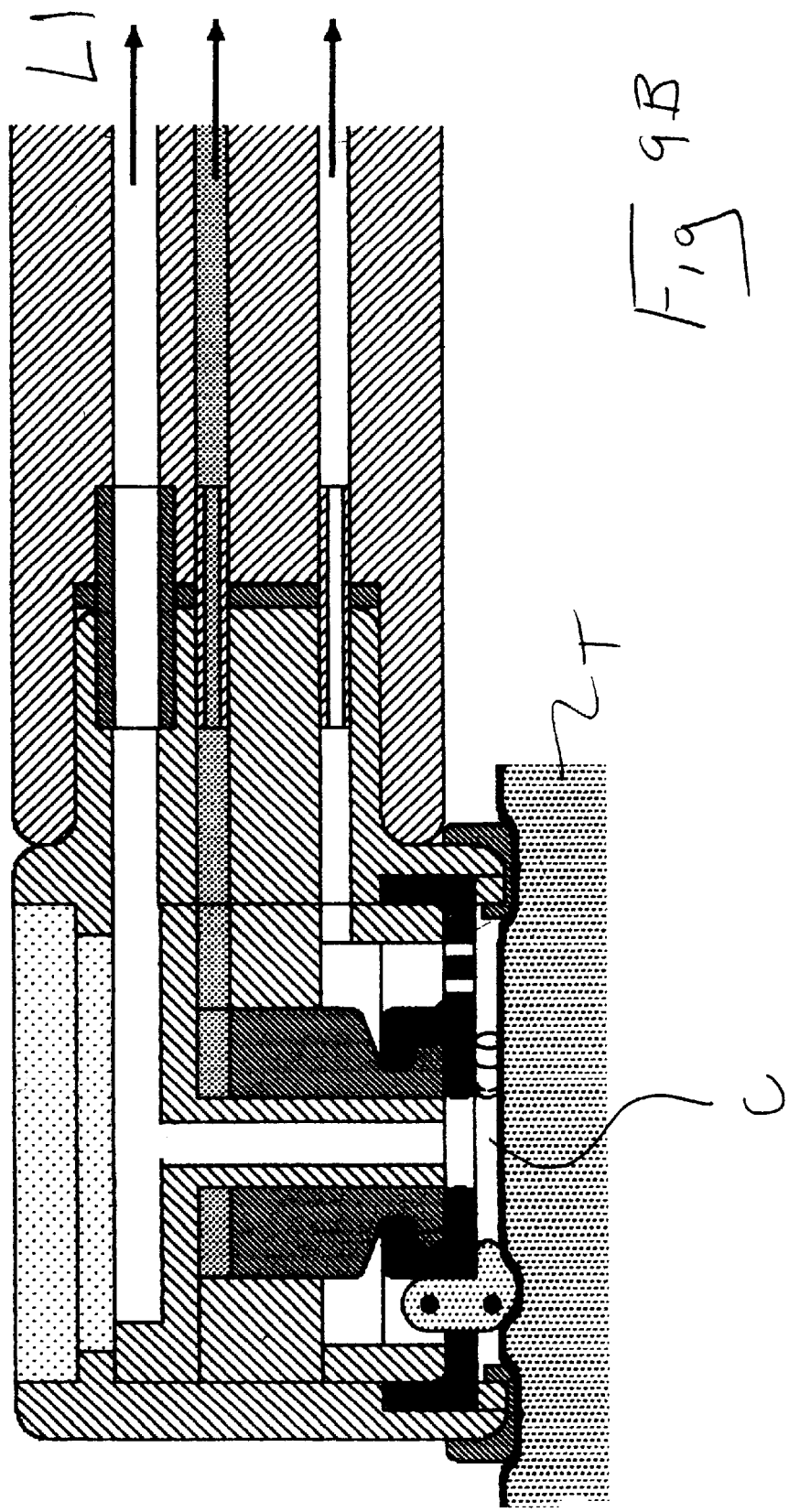

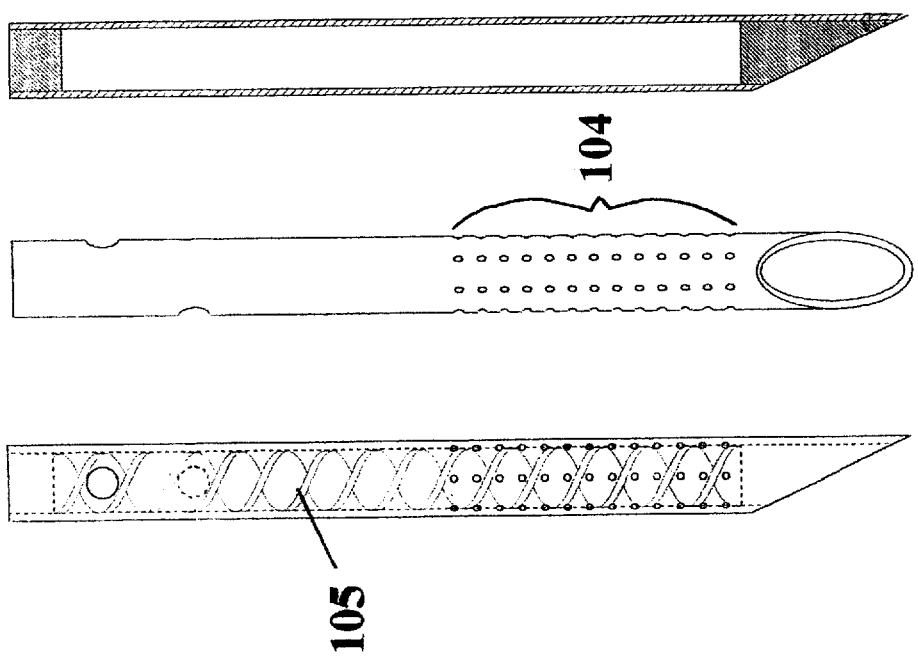

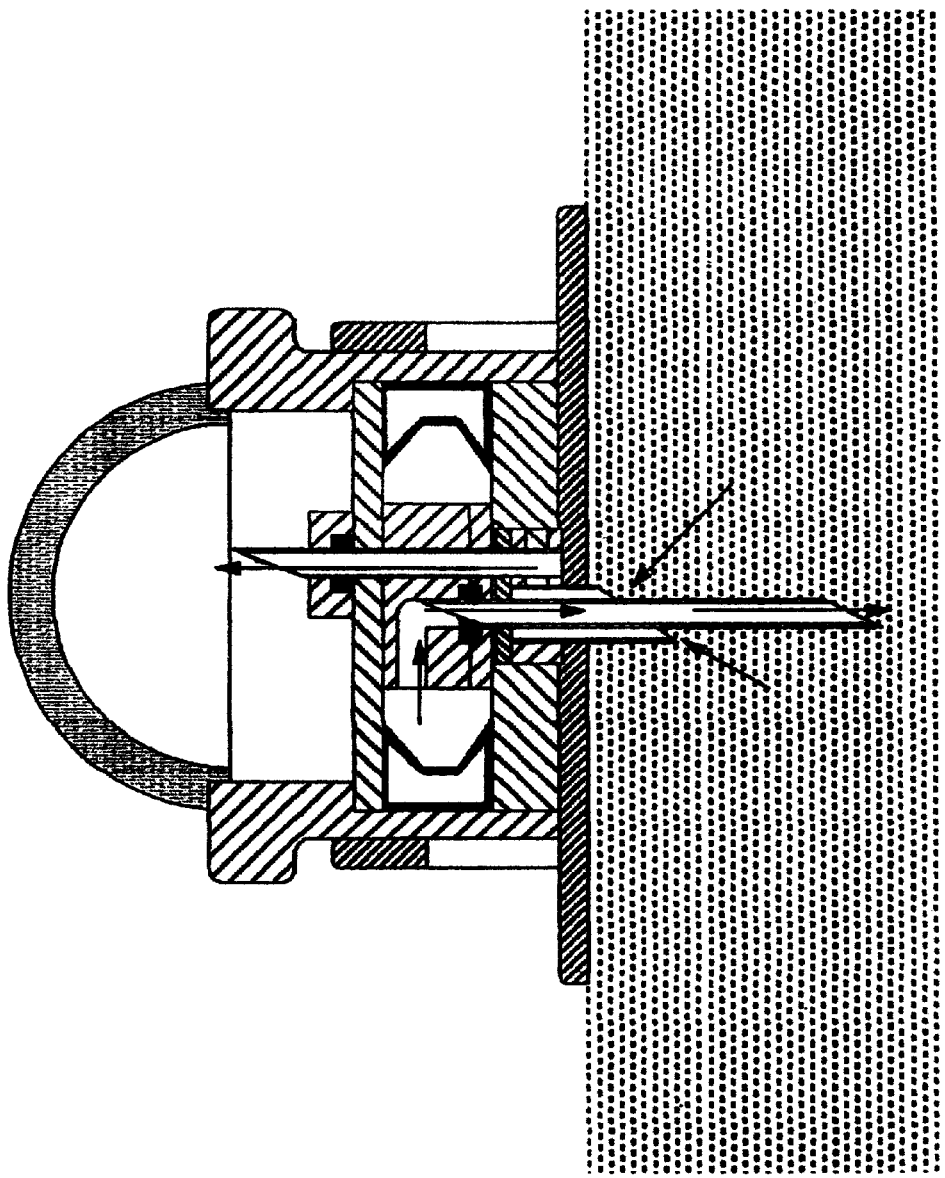

AUTOMATED COMPULSORY BLOOD EXTRACTION SYSTEM

STATEMENT OF CONTINUING INVENTION

The present application is a Continuation-In-Part of U.S. Provisional Patent Application Serial No. 60/017,633, filed May 17, 1996, entitled "Automated Compulsory Blood Extraction System", listing as the inventor Christopher L. Rambin.

FIELD OF THE INVENTION

This invention relates to a method and apparatus for the treatment of thrombosis, venous insufficiency, stimulation of blood circulation, and the like, and in particular to an Automated Compulsory Blood Extraction System (ACBES) configured to provide an efficient and safe means for the measured extraction of blood utilizing a device providing, in effect, an artificial leech, but without the infection, control, care, and other limitations associated with the medicinal leech.

The preferred embodiment of the present invention utilizes recent micro technological advances to provide a micro mechanical device which mimics and improves upon the bloodletting properties of the medicinal leech utilizing a micro mechanical valve, drive pump, and micro sensor arrangement cooperating with a tertiary jaw array having teeth situated thereon.

The preferred embodiment of the present invention contemplates an extraction device which may have a head size of one centimeter or less, and which may be utilized in number about the affected area of the patient to provide controlled, precision, pulsed blood extraction via vacuum induction, supplying a controlled dosage of anticoagulant, histamine anesthetic, or the like.

Alternative embodiments of the present invention includes an independent, single needle, stationary design configured primarily for emergency use, a multi-needle piston design, a large extraction area array design including concentric needles of adjustable depth, and a deep extraction needle design, providing various configuration blood extraction systems designed for a variety of specialized operations.

BACKGROUND OF THE INVENTION

While medicinal leeches (Hirudo Medicinalus) have been utilized for treating a variety of ailments for hundreds of years, medical science has yet to provide a device which surpasses the effectiveness of the leech for certain applications, hence their continued extensive use in medicine today for stimulating circulation and related treatments.

Even today, the most commonly reported method for restoring circulation to damaged tissue has been through the use of medicinal leeches. In spite of the limitations, the leech has remained the best and only means of compulsory blood extraction for the purpose of stimulating circulation in tissue having restricted circulation.

The lack of control variables such as flow rate, flow pressure, vacuum magnitude, fluid injection and total extraction volume limits the physicians ability to tailor the extraction via vacuum induction, supplying a controlled dosage of anticoagulant, histamine anesthetic, or the like.

Alternative embodiments of the present invention include an independent, single needle, stationary design configured primarily for emergency use, a multi-needle piston design, a large extraction area array design including concentric needles of adjustable depth, and a deep extraction needle design, providing various configuration blood extraction systems designed for a variety of specialized operations.

BACKGROUND OF THE INVENTION

While medicinal leeches (Hirudo Medicinalus) have been utilized for treating a variety of ailments for hundreds of years, medical science has yet to provide a device which surpasses the effectiveness of the leech for certain applications, hence their continued extensive use in medicine today for stimulating circulation and related treatments.

Even today, the most commonly reported method for restoring circulation to damaged tissue has been through the use of medicinal leeches. In spite of the limitations, the leech has remained the best and only means of compulsory blood extraction for the purpose of stimulating circulation in tissue having restricted circulation.

The lack of control variables such as flow rate, flow pressure, vacuum magnitude, fluid injection and total extraction volume limits the physicians ability to tailor the extraction process for each individual application. Also, bacteria in the leech gut the can be transferred to a patient, adding complications to an already critical state.

The leech is generally used only as a last resort for reestablishing circulation to tissue threatened with hypoxia due to the absence of blood flow. There are many cases where the leech would be used by physicians if it had reliable operation characteristics and there was no chance of infection.

Devices which may have some pertinence to the present, searched for invention may include:

U.S. Pat. No. 5,368,034 teaches a system for facilitating thrombolytic therapy including a sensor monitoring blood flow rate, and alarm means for indicating blood flow above a predesignated rate.

U.S. Pat. No. 5,163,926 teaches a suction metering and mixing device for collecting body fluids, including blood, and simultaneously mixing an anticoagulant therewith.

U.S. Pat. No. 5,037,407 teaches an "Electronic Monitoring System for Drainage Device" comprising a monitoring system for monitoring body fluids passing through, detecting and indicating when a bubble is sensed therein.

U.S. Pat. No. 4,998,919 teaches a "Thrombectomy Apparatus" comprising first and second lumens enveloping, and an additional chamber in the second lumen having a longitudinal passage for enveloping a safety change wire therein.

U.S. Pat. Nos. 5,141,501 and 5,163,926 teaches a "Suction Metering and Mixing Device" comprising a device having a chamber for controlling the flow of anticoagulant into a suction wand, said wand further including a first suction tube, and second anti-coagulant tube.

Notwithstanding many attempts at replacing the leech with mechanical devices and the like, some of which are taught above, medicine has yet to find a suitable replacement.

An article published in *Medical Update* (May 1995) by E. W. Brown estimates 65,000 leeches are used each year for medical purposes. These applications are restricted to the limited "last resort" cases, since the leech has an inherent unreliability and promotes a possibility of infection.

As indicated the utilization of a medicinal leech in medicine has its shortcomings; for example, the medicinal leech can be used for relieving vascular occlusion but not arterial occlusion, since the latter case has a high risk of infection from bacteria transferred from the leech. Thus, an artificial leech which would be sterile, thus can be used in arterial occlusion cases. This limitation of medicinal leeches, as well as other cases reported in literature, indicate the number of case applications for the artificial leech is expected to expand beyond the current range of medicinal leech use. Brown (1995) reports that leeches are used for over 5000 cases per year. This number would be greater if the treat of infection and the unreliable nature of the creatures could be eliminated.

The medicinal leech as seen a resurgence in use for practical application as a means of restoring circulation to damaged tissue. In the 1960's, British surgeons began applying the leech to post operative regions of sutured tissue to encourage blood flow. After surgery, some tissues will not be able to drain blood due to venous blockage. The practice became prevalent in America after Dr. Joe Upton used leeches to restore circulation to a reattached ear in 1986. The leeches were credited with saving the ear since the low drainage pressure of venous system was unable to restart circulation. Publication of this success brought the acceptance of leeches as an essential means of restoring circulation to damaged limbs.

Leeches are common through out the world. They all are parasites that prey on warm blooded animals. The medicinal leech (hirudo medicinalis) is of particular use because of its size and the minimal wound it produces. A leech can survive for nearly a year without feeding. Medical practice has found that six months of starving a leech leaves them strong enough to attach themselves immediately upon introduction to the patient.

The leech has the following desired characteristics for the surface extraction of blood:

1) the leech can be placed near the wound site by a medical attendant,
2) the size of the leech head (about 1 cm in diameter) allows for close attachment at the edge of a closed wound,
3) the leech jaws scratch a shallow wound in the skins surface which produces no scaring,
4) the leech injects a histamine and an anticoagulant that aid in opening clogged capillaries,
5) the blood drained by the leech is drawn mainly from the venous capillaries, when finished, the leech detaches itself.

The overall advantage of the leech is that it draws the venous capillary blood that results in the unclogging of the local circulatory passages and thus restores blood circulation to the damaged tissue.

There are limits to the use of leeches due to their arbitrary behavior and desire to only feed themselves and then leave the host. The limits on leech use include:

1) the leech can be placed close to a desired site but not placed exactly at a particular point,
2) leeches carry a bacteria that can infect a patient and lead to further complications as described by Haycox et al in 1995,
3) the possibility of infection limits the types of cases and patients the leeches may be used on;
4) the rate of blood extraction can not be controlled;
5) the leech only drinks about 2 cc of blood then detaches requiring multiple leech use in succession for extended blood extraction,
6) the physician has no feedback information from the leech to verify the restoration of circulation.

Utilization of the Leech in Medical Procedure

In cases of poor circulation, the medicinal leech (Hirudo Medicinalis) is applied to the skin over the effected area allowing the creature to attach itself and withdraw blood at will. The leech is seeking only to feed itself but in the process it benefits the patient by encouraging blood flow into a restricted region. The damaged tissue is typically the result of an amputation. A detached limb can be surgically reattached without fully enabling the circulatory system. There are other means of tissue damage that lead to decreased circulation. Without the circulatory system fully functioning the tissues are insufficiently supplied with nutrients leading to tissue death.

Historically, the medicinal leech was used to extract what was believed to be bad blood from an ill patient. This misconception has been corrected in modern times. The use of the leech to withdraw blood from a tissue region with poor circulation has proven to be essential for saving damaged and reattached tissue.

Only one species of leech is used in medicine. This creature has been well studied to provide doctors with reliable information on leech actions. The leeches are raised in a sterile environment. A leech can live for months without being feed. When the leech reaches a certain age, it is considered to be the right size for use in blood extraction. A starving leech is used to ensure quick action. The leeches are used on a patient only once, then they are destroyed.

The Functional Leech Anatomy and Its Operation in Blood Extraction

Referring to FIG. 7, the leech head has four main sections: the lip which forms an air tight seal, the buccal tissue region which supplies secretion to the attachment site, the jaws that form a Y shaped wound and the throat which expands to form a vacuum and drain the extracted blood. When attached the leech head is about one centimeter in diameter. Each jaw piece is roughly one to two millimeters in length with about 50 teeth.

The application of a leech to preform blood extraction in a clinical environment occurs as follows:

1) A starved leech is removed from its colony.
2) The leech is placed on the skin at the site intended for blood extraction.
3) The leech attaches to the skin by a posterior sucker.
4) The leech attaches its anterior sucker to the skin. (The anterior end is the leech's head that has the jaw, throat and secretion tissue.)
5) A low pressure region (vacuum) is formed in the leech throat by muscular expansion.
6) The tissue around the jaw secretes a liquid form of an anesthetic, histamine and anticoagulant.
7) The jaw (all three of the jaw sections) is pressed against the skin surface and is "rocked" to produce a sawing action.
8) A wound is formed in the skin by the sawing action.
9) The low pressure around the center of the jaw draws blood from the wound.
10) After the throat cavity is filled, the leech ingests the crop.
11) The pressure relief from the injection allows a back flow of the excreted fluid into the wound. (The vacuum is reduced over the wound during injection but is not entirely released.)
12) The jaw is maintained in pressure against the skin with teeth extending into the wound without completely filling the opening.

13) The jaw sawing action, fluid excretion, and throat vacuum are continued until the throat cavity fills again.

14) The crop is ingested.

15) The processes are repeated until the leech is full.

16) The leech detaches and is removed. (The leech takes less than one hour to fill itself.)

17) The wound continues to bleed for several hours.

18) Another leech can be placed on the extraction site.

It is noted that some authors claim that the sawing action of the jaw occurs only in the initial phase of attachment to produce a wound. None of the authors offer proof of this assertion. Some reason that the action would reduce the seal around the mouth. Others state that the force of the vacuum would restrict any motion. My reasoning is that jaw motion during extraction maintains the wound clearance without increasing the size of the wound. Also, the anticoagulant helps keep the blood flowing but is not the only means of maintaining flow. For these reasons, the AHM (Artificial Hirudo Medicinalis) is designed for simultaneous extraction, secretion and jaw motion.

AIR PUMPS

Air pumps of varying size and quality are common in modern society. Vacuum pumps are mainly used for industrial and scientific applications. In medicine, pumps are used for fluid transfer and as actuators for mechanical instruments. Multi-chambered pumps are available to deliver different pressures simultaneously. One such pump is used to drive a therapeutic sleeve for mechanically massaging anus and legs (Healthtronics Medical Equipment Corp., Dallas, Tex.). These pumps are digitally controlled to provide precise time varying pressures. While such pumps are freely available, none are known to be utilized in conjunction with an artificial leech, as contemplated in the system of the present invention.

MICRO MECHANICAL TECHNOLOGIES

Machining technology over the past decade has lead to a new field of fabrication technology know as Micro Electro Mechanical Systems (MEMS). These new fabrication methods are able to produce mechanical parts with dimensions on the order of 50 um and resolutions of less than 1 um. Though the leech is about 5 cm long and the attached head is about 1 cm in diameter, building an artificial leech would require the use of micro technology, since the leech jaws and teeth are very small and require actuation while a vacuum is present. To date, such a design is believed unattained by others.

In 1995, Smoot and others published on article in the *Journal of Reconstructive Microsurgery,* describing the application of a small vacuum vessel over a puncture wound in a rat. The wound was placed on a site of tissue re-attachment to show the effect of force blood extraction. The wound was washed during extraction with a saline solution. Smoot states the need for an artificial leech since biological "leeches increase the possibility of infection . . . ". Also, the brief feeding time of a single leech is not sufficient to completely remove congestion in the effected tissue. For these reasons, the authors promote the use of mechanical means for compulsory blood extraction.

The Vacuum Shunt

Medical researchers sometimes refer to a "mechanical leech" when they describe the use of a vacuum shunt to remove fluid from a site of reconstructive surgery. The device is not at all like a medicinal leech. It has the similarity of extracting blood from a body cavity by reduced pressure, but is not a leech in the sense of this invention.

Lastly, a medical instrument maker in France named Luer sold a so-called "artificial leech" in the 1860's comprising a scarifier and two suction tubes, thus not simulating a leech at all, but instead providing a somewhat primitive suction means for drawing blood from the patient.

Thus, while the prior art has contemplated devices which evidence attempts at providing a replacement for the leech, it is submitted that a suitable replacement is not evidenced in prior teachings.

GENERAL SUMMARY DISCUSSION OF THE INVENTION

Unlike the prior art, the present invention provides a blood extraction system which provides the effectiveness of the medicinal leech, but without the limitations thereof The idea for this system began in July of 1992 when the inventor first saw a CNN news report on the use of leeches in medicine. The report showed a leech on the tip of a surgically reattached toe. The leech was necessary to reestablish blood flow into the previously severed limb.

After studying the anatomy and operation of a leech, it became clear to the inventor that a mechanical device could be built that would preform all of the functions of the leech, and could be monitored and controlled by the user, utilizing micro miniature design and manufacturing techniques. With the availability of electronic control systems to operate a pump drive, the devices proposed as a leech replacement can be used with detailed feedback data for analysis by the attending physician.

The Artificial Hirudo Medicinalis (AHM) forming the ACBES of the present invention consists of two major sections. The first is the AHM attachment device that mechanically functions as a biological leech head. The second is a pump driver that operates the AHM device. The pump is easily manufactured using current pump technology common in the medical field. The AHM device, however, is believed unique at present, requiring fabrication techniques using newly developed micro technology that can produce miniature device structures with micrometer tolerances.

A special hose with three channels connects the AHM device to the pump driver. This hose can be manufactured using current technology developed for the production of micro tubing.

The AHM could not have been built previously due to the lack of fabrication methods. Recent advances in micro fabrication techniques has enabled the production of these devices. Some aspects of the structures can be produced by precision engineering, however the major parts can only be mass produced cost effectively by the new methods. For example, the jaw pieces are flat (0.25 mm thick) and have teeth with 0.1 mm dimensions. The new LIGA process of x-ray lithography and electroplating allows for the mass production of these parts without degradation of the master image.

The advances of micro electronics since the 1960s has resulted in smaller and faster computational processors and controllers. These processors have the ability to preform calculations and control electro mechanical devices. Mechanical devices have been built using the methods for the fabrication of microelectronic, however, the scope of application is very limited. New methods designed explicitly for the production of micro machines have been advanced since the early 1980s.

Recent advances in micro mechanical systems have produced miniature mechanical valves to control gas and liquid flow. Micro pumps have been developed based on the valve designs. These devices are electrically operated. In concert with the valve development is the production of micro sensors. For fluid applications, pressure and flow rate are essential parameters. Sensors for measuring these two physical quantities have also been produced.

The availability of the above mentioned devices opens the possibility for the construction of a microfluidic system. A specific application of a fluidic system is the mechanical leech.

Medical Application of the AHM

There are no other devices on the market that preform the function of the medicinal leech. The AHM device of the present invention is designed to completely replace the use of leeches in medicine. Also, the use of blood extraction can be expanded to a more common use due to the dependability and portability of the devices. An artificial leech must be designed to have the following characteristics that mimic the medicinal leech:

1) Vacuum induction
2) Adhesion to the skin
3) Opening of a wound
4) Supply of anticoagulant, histamine and anesthetic
5) Continual pulsed blood extraction (pulsed refers to the drinking action)
6) Release from the skin An example of the utilization of the AHM in the above medical procedure could include, for example:

1) placing the extraction chamber of the AHM on the skin at the site intended for blood extraction;
2) initiating a vacuum or other adhesion means in the vicinity of the extraction chamber, in such a manner as to affix the AHM to the skin;
3) dispensing in the vicinity of the exaction chamber an anesthetic, histamine and anticoagulant;
4) initiating mechanical jaw sections against the skin in the vicinity of the extraction chamber to rock, producing a sawing action;
5) forming an incision in the skin by way of the sawing action;
6) initiating a low pressure suction in the vicinity of the extraction chamber, drawing blood from the wound;
7) relieving the suction, allowing the dispensed medication to be assimilated by the wound;
8) continuing sawing action of the jaw, fluid excretion, and increased and decreased low pressure vacuuming of the area in a pulsed fashion;
9) removing the desired fluid from the patient, stimulating circulation in the area of the wound;
10) removing the device;
11) allowing the wound to continue to bleed for a period of time following removal of the device;
12) re-initiating steps 1–11 until the desired treatment is completed.

It is therefore a an object of the present invention to provide an Artificial Hirudo Medicinalis (AHM) which provides controlled, sanitary extraction of fluids from a patient in such a manner as to limit infection, scarring, or discomfort, while promoting monitored, controlled stimulation of the circulatory system of the patient in the vicinity of the wound.

It is another object of the present invention to provide an AHM which requires little in the way of maintenance, is relatively easy to implement, and which provides a more sanitary, controlled treatment therapy when compared to the prior art.

It is still another object of the present invention to provide an Automated Compulsory Blood Extraction System which mimics in certain ways the bloodletting process of the medicinal leech, but without the care requirements, sanitary problems, control, monitoring obligations, and general patient phobia associated with the medicinal leech.

It is still another object of the present invention to provide specialized Automated Compulsory Blood Extraction Systems which are designed for particular specialized treatments.

It is an object of the present invention to provide an Automated Compulsory Blood Extraction System utilizing a single or plurality of AHM's to provide computerized, monitored removal of fluids from venous inhibited tissue area of a patient.

Lastly, it is an object of the present invention to provide a micro mechanical device which provides a suitable replacement for the medicinal leech, implementing accepted medical techniques utilizing state of the art micro mechanical engineering and electronics.

BRIEF DESCRIPTION OF DRAWINGS

For a further understanding of the nature and objects of the present invention, reference should be had to the following detailed description, taken in conjunction with the accompanying drawings, in which like parts are given like reference numerals, and wherein:

FIG. 3A illustrates a perspective view of the ACBES system of the present invention, illustrating the AHM of FIGS. 1A and 1B mounted upon a reattached thumb of a patient, and connected to a vacuum pump/control device.

FIG. 5A illustrates a close-up view of a directional tooth of the directional jaw blade of FIG. 5.

FIGS. 6A–6H comprise graphs, each illustrating the time dependent pressure variation curves for each phase of operation of the AHM of FIGS. 1A and 1B, each of whic are illustrated in the flow chart of FIG. 6.

FIGS. 9A–9F illustrates the application of an alternative embodiment of the AHM of FIGS. 1A and 1B, and the various steps in extracting blood from the tissue of a patient.

FIG. 13B provides side, partially cut-away, and cross sectional views of the needles and casings utilized in the invention of FIG. 13A.

FIG. 14A provides a side, partially cut-away, partially cross-sectional view of a seventh, independent needle stationary design configured to be self-contained and for utilization in emergency situations and the like.

FIGS. 14B–14C provide side, partially cut-away, partially cross-sectional views of the invention of FIG. 14A, illustrating operational phases of the device utilized in a compulsory blood extraction from a patient's tissue.

DETAILED DISCUSSION OF THE INVENTION

Figure 1A:
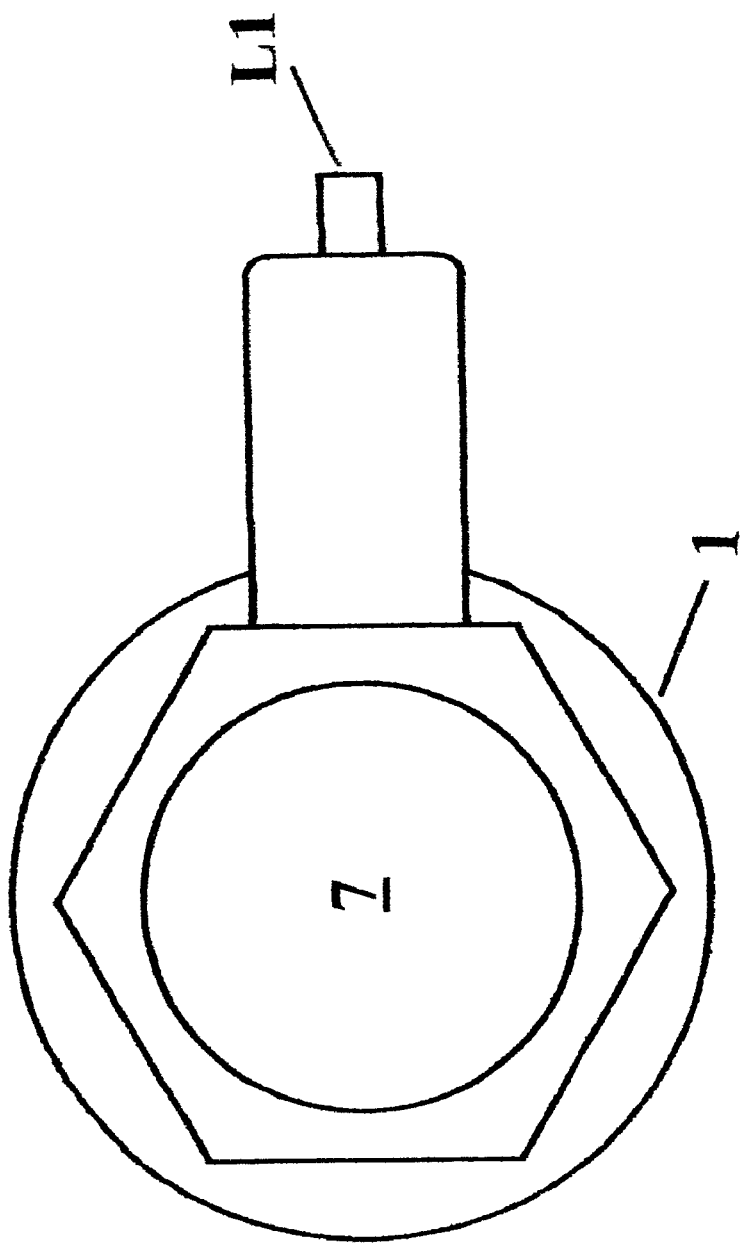
FIGS. 1A and 1B illustrate top and side views, respectively, of the Artificial Hirudo Medicinalis (AHM) of the preferred embodiment of the present invention.
Figure 1B:
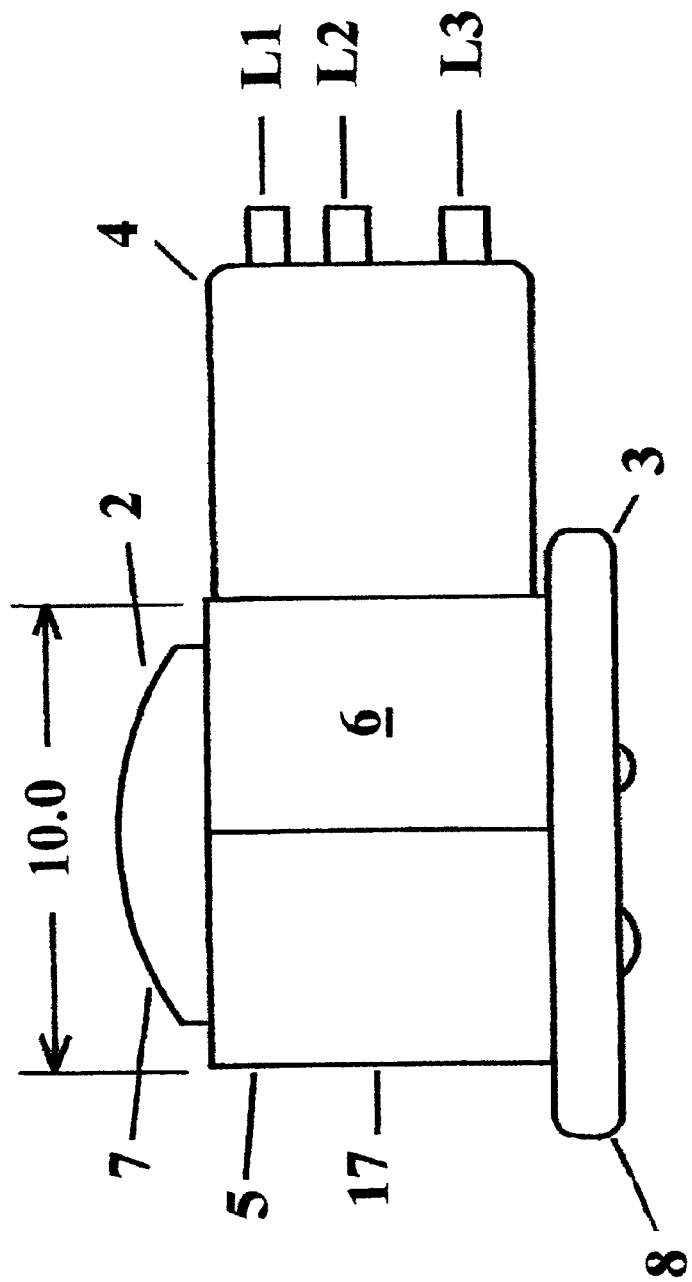

Referring to FIG. 3A, the preferred embodiment of the automated compulsory blood extraction system (ACBES) of the present invention is utilized in a manner consistent with the treatment of inhibited venous functions, particularly circulatory limitations brought about by physical trauma, disease, and the like.

As shown in the figure, an exemplary situation wherein the present system may be useful might comprise where a patient 25 has suffered a trauma to the thumb 26, which has been reattached 27. In such a situation, reestablishment of circulation of blood is critical, as impaired or no circulation to a portion of the reattached tissue will result in degeneration of same. Such has been the usefulness of the medicinal leech, as the leech is attached at generally an area of the tissue on the skin where circulation is impaired, and the leech, extracting blood from the tissue, provides a low pressure area where blood from surrounding tissue is drawn, thereby stimulating circulation. Further, the leech includes an anticoagulant agent in its saliva, which further stimulates the free flow of blood in the impaired tissue.

In the present invention, an AHM 21 is attached to the patient's impaired tissue, and is powered and controlled by a control box 20, which functions may include, for example, providing a dosage of medication, which may include, for example, antihistamine, anti-coagulant, anesthetic, or the like, and which may provide pneumatic, electric, cable, or other power means to power the AHM, suction means for drawing blood from the impaired tissue, monitoring means to monitor the state and performance of the system, and timing means for providing appropriate interval timing for performing the method of the present invention, all of which will be further disclosed infra. Lastly, the control box 20 interfaces with the AHM 21 via hose 22 having first 23 and second 24 ends, the first 23 end connected to the control box 20, the second 24 end connected to the AHM 24.

Referring to FIGS. 1A–1B and 2A–2B, and 3B the preferred embodiment of the AHM 1 of the present invention comprises a housing 17 which may be formed of, for example, stainless steel or the like, the device further including a top 2, a bottom 3 defining an underside, a first end 4 having vacuum L1, hydrostatic piston drive L2, and medication supply L3 lines. Further provides with the device is a second end 5 distal the first end, and a side 6. The housing of the shown embodiment may be, for example, about 10 millimeters wide.

Located at the top 2 of the preferred device may be a viewing dome 7 or window, allowing the operator to monitor the passage of fluids there through.

Located at the bottom 3 of the preferred embodiment is the base 8, which has formed therein an extraction chamber 10 having a periphery formed by a sealing lip 9 which functions as a fluid sealing gasket when used, as will be discussed infra.

The extraction chamber of the preferred embodiment of the present invention may measure about 1 centimeter, for example. Of all the leeches available for blood extraction, only one has been successful on humans. This is not a matter of chance, but a result of centuries of leech application (though for the wrong reasons). The leech that became Hirudo Medicinalis has a particular size of head that is about 1 cm in diameter. Because of the density and elastic properties of the skin and veins, this 1 cm size has the correct circumference to area ratio that provides a sufficient region for a wound without cutting off the circulation by too much stress around the parameter.

Thus, the 1 cm AHM is, at this time, believed to represent the best natural design. At this time, it is anticipated that sizes which vary substantially from these dimensions may require too much vacuum that will result in shutting off the local circulation of the patient, and leading to over dosing of AHA (antihistamine and anticoagulant).

Figure 2A:
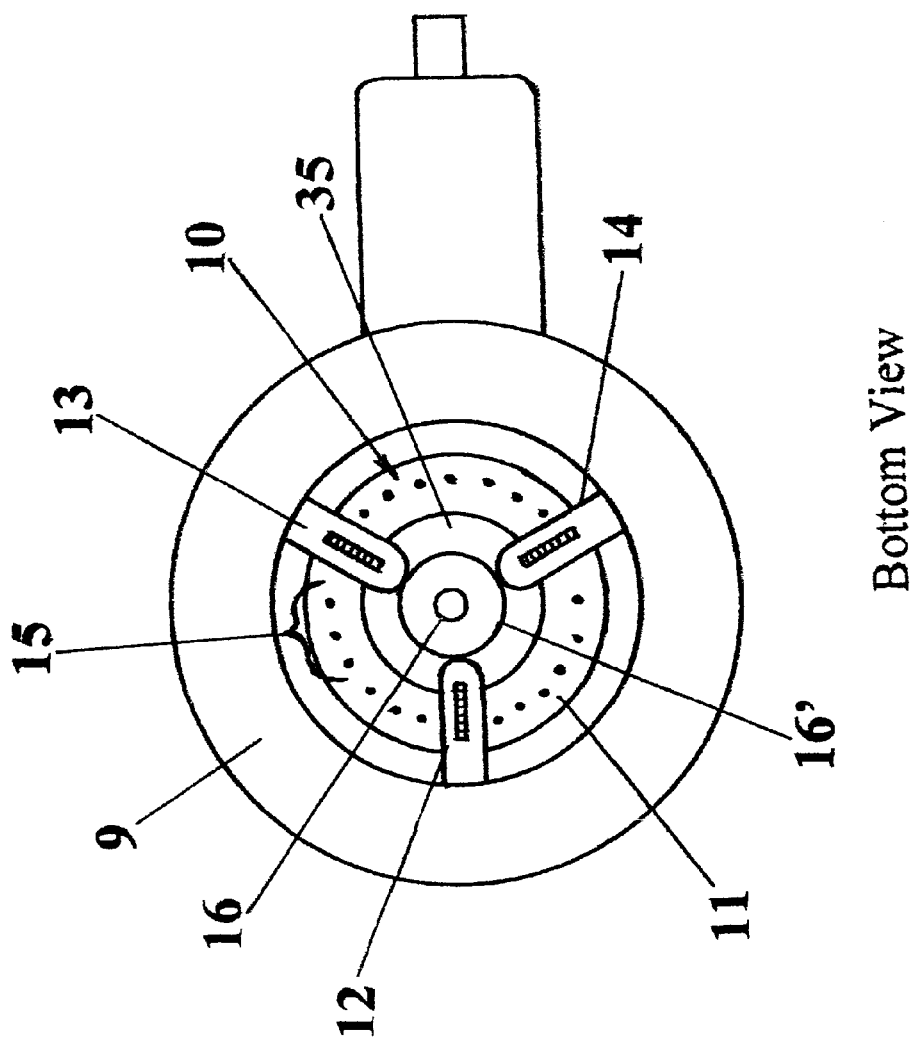
FIGS. 2A and 2B illustrate bottom and end views, respectively, of the preferred embodiment of the AHM of FIGS. 1A and 1B.
Figure 2B:
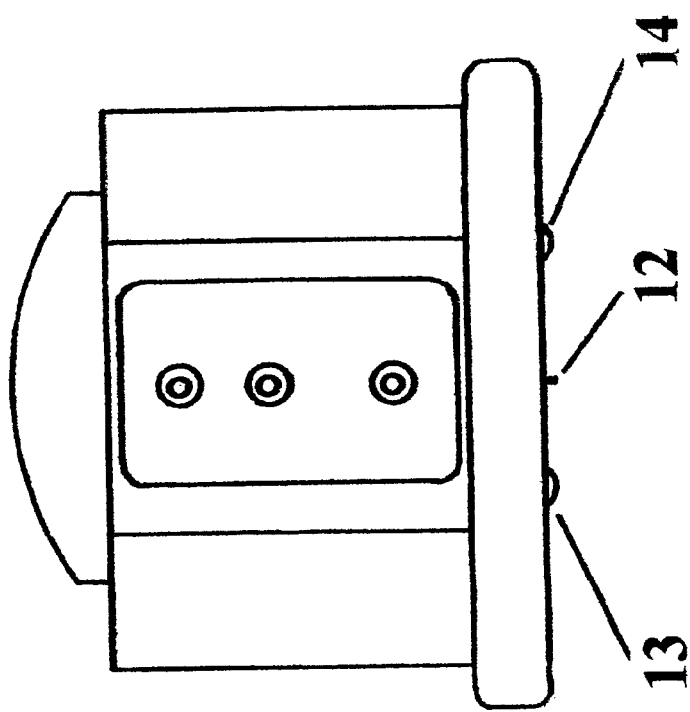
Figure 8:
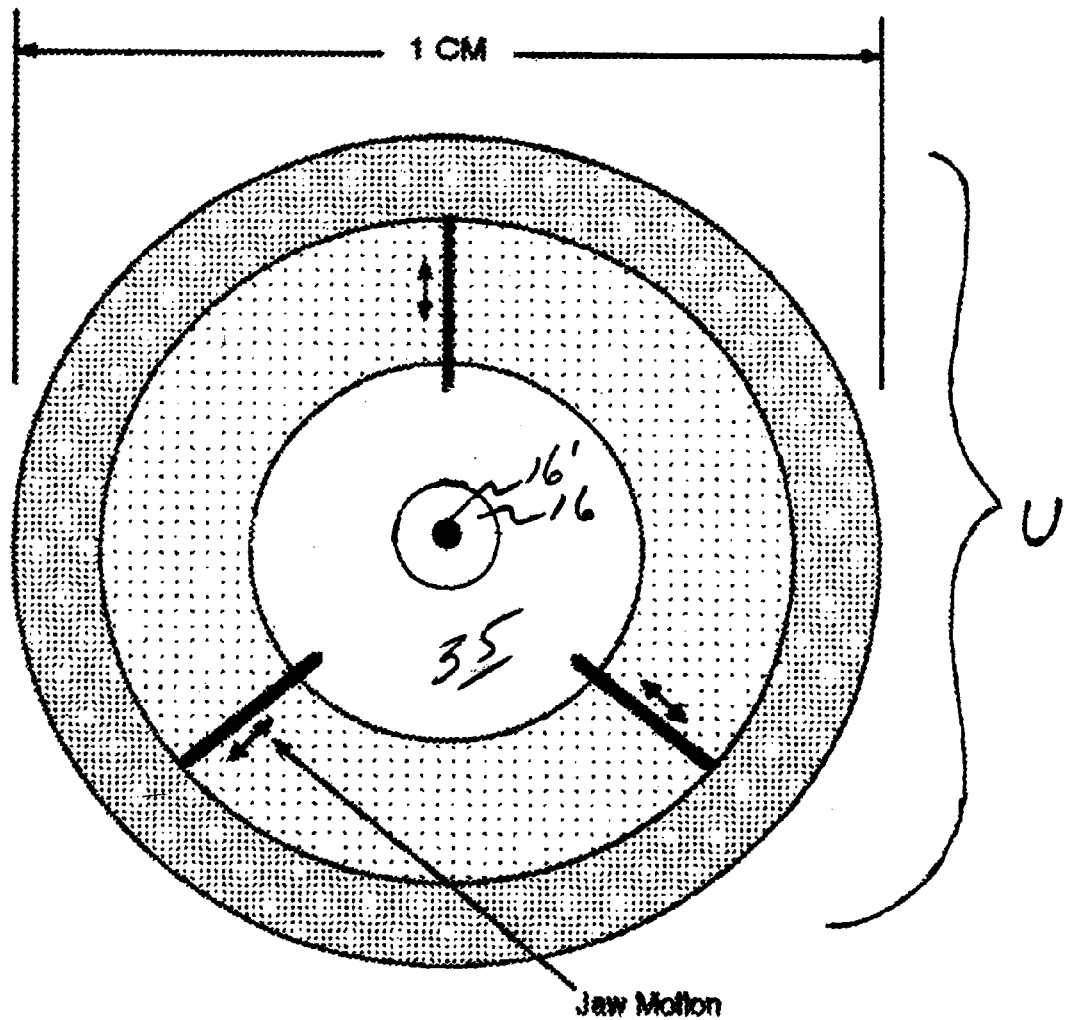
FIG. 8 is a bottom view of the AHM of the invention of FIGS. 1A and 1B, illustrating the area of the leech which contacts directly with the tissue of the patient to be treated, and further illustrating the various component regions associated therewith.

Referring to FIGS. 2A and 8, the underside U of the present device comprises three primary regions, as shown, an outer pressure seal formed by lip 9, which sealingly envelopes the periphery of the extraction chamber 10 which may be, for example, about 2 millimeters deep.

Emanating from the periphery of the suction conduit to generally the lip 9 is a diaphragm 11 formed in this embodiment of a flexible material which may include, for example, a non-elastic, single metal hexagon of electromold formed metal such as, for example, as is utilized in iron nickle-iron plating, as is done by Dynamics Research of Wilmington, Mass., or, alternatively, a diaphragm formed of a compound having elastic properties (such as silicon, rubber, or the like) and criteria which would fit in the present system.

The diaphragm may include a plurality of medication drainage holes 15 which may measure, for example, about 1 mm, but whose size can vary depending upon the size of the unit, number of orifices desired, the fluid passing there through, the type of treatment desired, the operating pressure of the unit, and other criteria. Medication drainage holes need not be formed in the non-flexible, metal hexagonal version, as the medicine could drain in slots formed above the jaw plates.

Forming the central area of the underside of the device is a suction conduit 16, which includes an opening 16' therein. Enveloping the outer periphery of the suction conduit 16 is beam 35 which pivotally engages first 12, second 13, and third 14, generally vertically situated jaw plates having first and second ends, the first ends engaging beam 35, the jaw plates also engaging diaphragm 11, lip 9, or the base 8 in pivotal fashion at a connection point C (shown engaging diaphragm), such that the jaw plate may pivot or rock from linear pressure or tension from beam 35, as will be more fully discussed infra.

Each of the jaw plates 12, 13, 14 are shown supported by a j-beam 12', 13', 14', respectively, having first and second ends, the first end engaging the base of the housing, the second end supporting a jaw plate and engaging beam 35. The j-beams of the jaw plate must be able to bend repeatedly a maximum of 15 degrees out of plane. The three j-beams provide the elastic recoil tension which return the Jaws and Piston to their starting position. Thus, actuation of the device is through the forward drive pressure in the second line which forces an internal downward, engaging beam 35 (which may be part of the piston), bending the j-beams and driving the jaw plates in to a patients skin. The pressure is reduced and the beam tension presses the Piston upward driving the piston fluid back into the pressure hose, as will be more fully discussed infra.

The tension from the j-beams depends on the jaw plate thickness and the width of the j-beams. Currently, the j-beams are shown to be one millimeter wide and the plate is 0.25 millimeters thick. Should we find that a greater recoil force is necessary, the beams may be widened.

The bending of the j-beams will produce some curvature and thus stress on the jaw and any jaw clip which might be employed to hold the jaw plate to the j-beam. Such a jaw clip may be adhered to the jaw plate beam by a semi-elastic adhesive.

The jaw plate is design to provide a means of mounting the jaws in a triangular arrangement in a precise configuration, in some ways mimicking the layout of the mouth of the medicinal leech.

Some exemplary jaw plate characteristics are:

The inner edges are about 1 mm for the mount center.

The jaw slit is about 1 mm from the beam's inner edge.

The outer diameter of the mount should be about 10 mm.

The inner diameter of the mount should be about 8 mm.

The shape of the j-beam can vary. The bean width depends on the strength of the material.

Figure 3B:
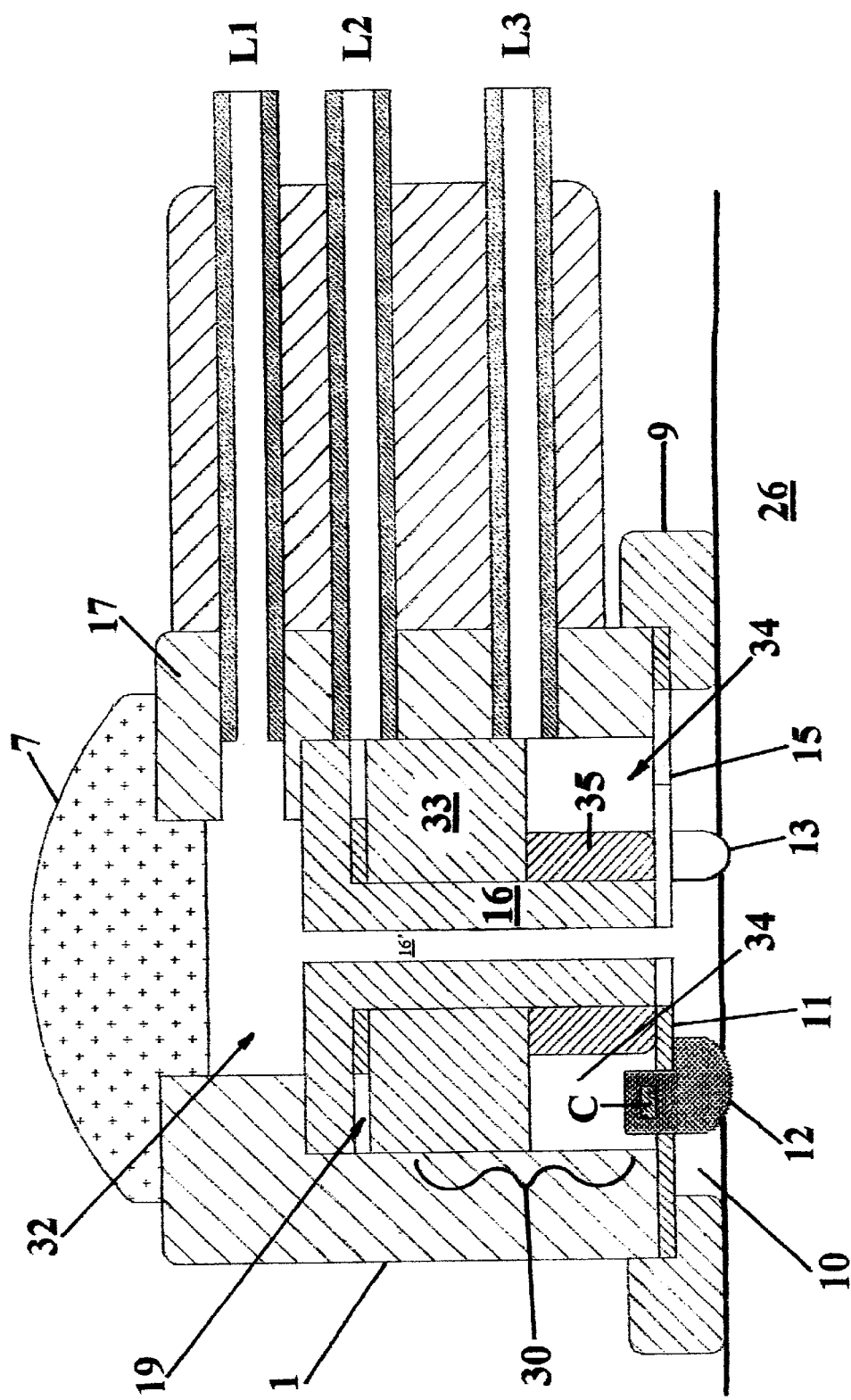
FIG. 3B illustrates a side, cut-away view of the preferred embodiment of the AHM of FIG. 3A.

Continuing with FIG. 3B, the housing 17 has formed therein, generally under the dome 7, a collection chamber 32 which may be viewed through dome 7, where the dome is transparent, the collection chamber communicating with line L1. Running from the collection chamber 32 and terminating at extraction chamber 10 is suction conduit 16 having suction passage 16' or opening formed there through, allowing suction generated from line L1 to be routed to the extraction chamber.

Situated between the collection chamber 32 and diaphragm 11 is a piston chamber 30 containing piston ring 33, configured to slidingly engage the outer periphery of suction conduit 16 and the inner wall of housing 17 in relatively fluid impermeable fashion, the piston ring 33 dividing the piston chamber 30 into upper and lower chambers, the upper chamber comprising a compression area 19 which communicates with L2, the lower chamber comprising a medication chamber 34 which communicates with L3 and diaphragm 11; further, the medication application orifices 15 formed in diaphragm 11 are configured to communicate medication dispensed within said medication chamber 34 via medication supply line L3 to the extraction chamber 10, and onto the patient's tissue 26.

Situated generally adjacent to the medication chamber 34, between the piston ring 33 and the diaphragm 11 and jaw plates 12, 13, is beam 35, which is configured to slidingly communicate linear movement from piston ring 33 to the jaw plates or jaw blades, positioning the jaw plates into contact with the skin and pivoting the jaw plates for providing serrating action to penetrate the patient 26 tissue, as will be more fully explained infra. It is noted that the beam may form a singe unitary structure with piston ring 33, as desired, and the piston may alternatively be in a shape other than a ring, depending upon the design of the system. Further, it is noted that the jaw plates may be formed in to a single structure, comprising supportive jaw beams which are connected, as will be more fully explained infra.

Operational Phases

Figure 6:
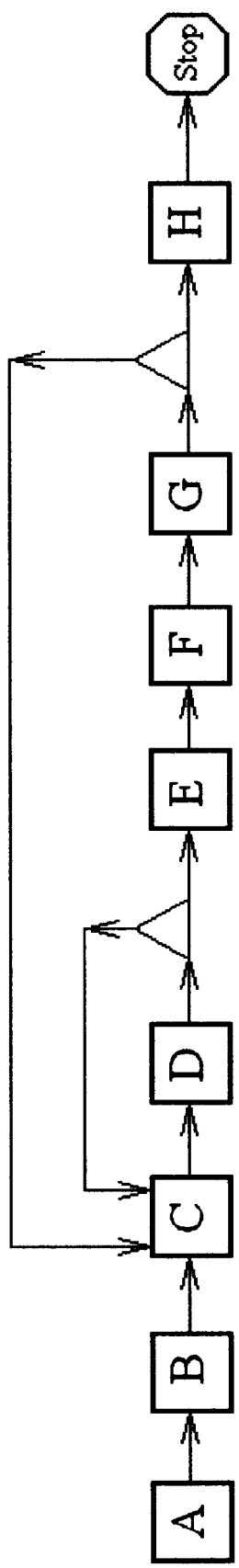
FIG. 6 is a flow chart illustrating the phases of operation of the AHM of FIGS. 1A and 1B.
Figure 6A:
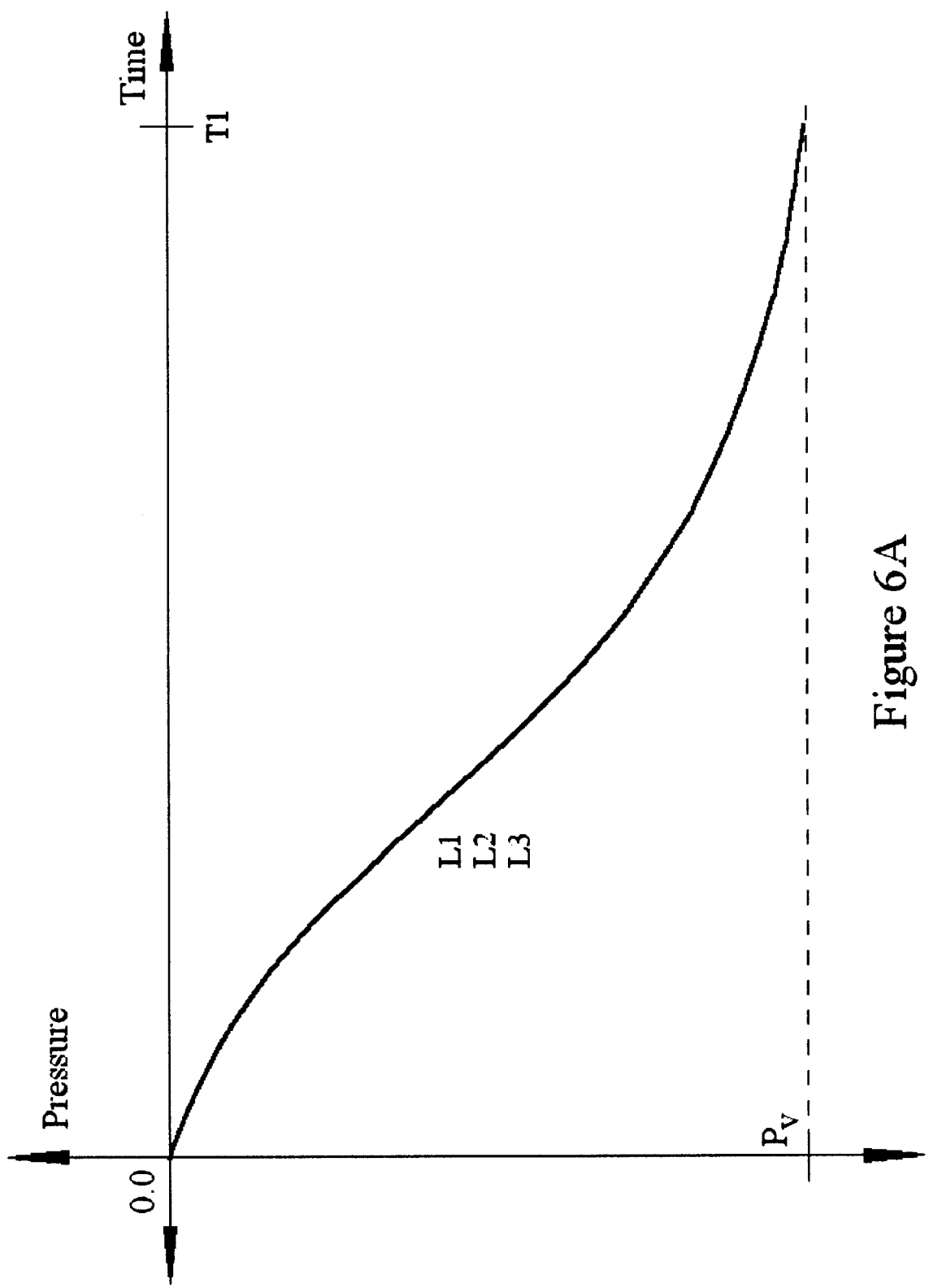
Figure 6C:
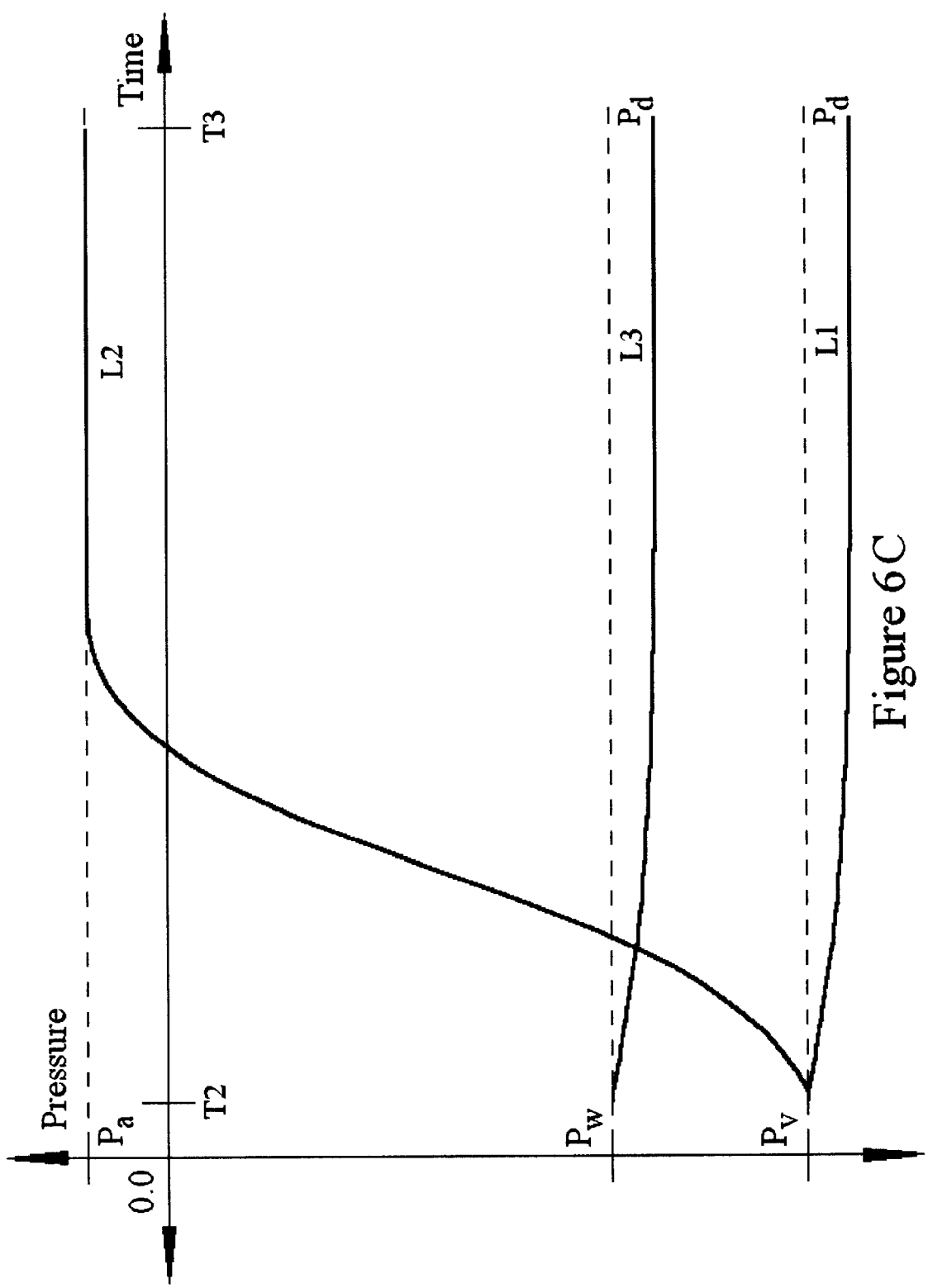
Figure 6D:
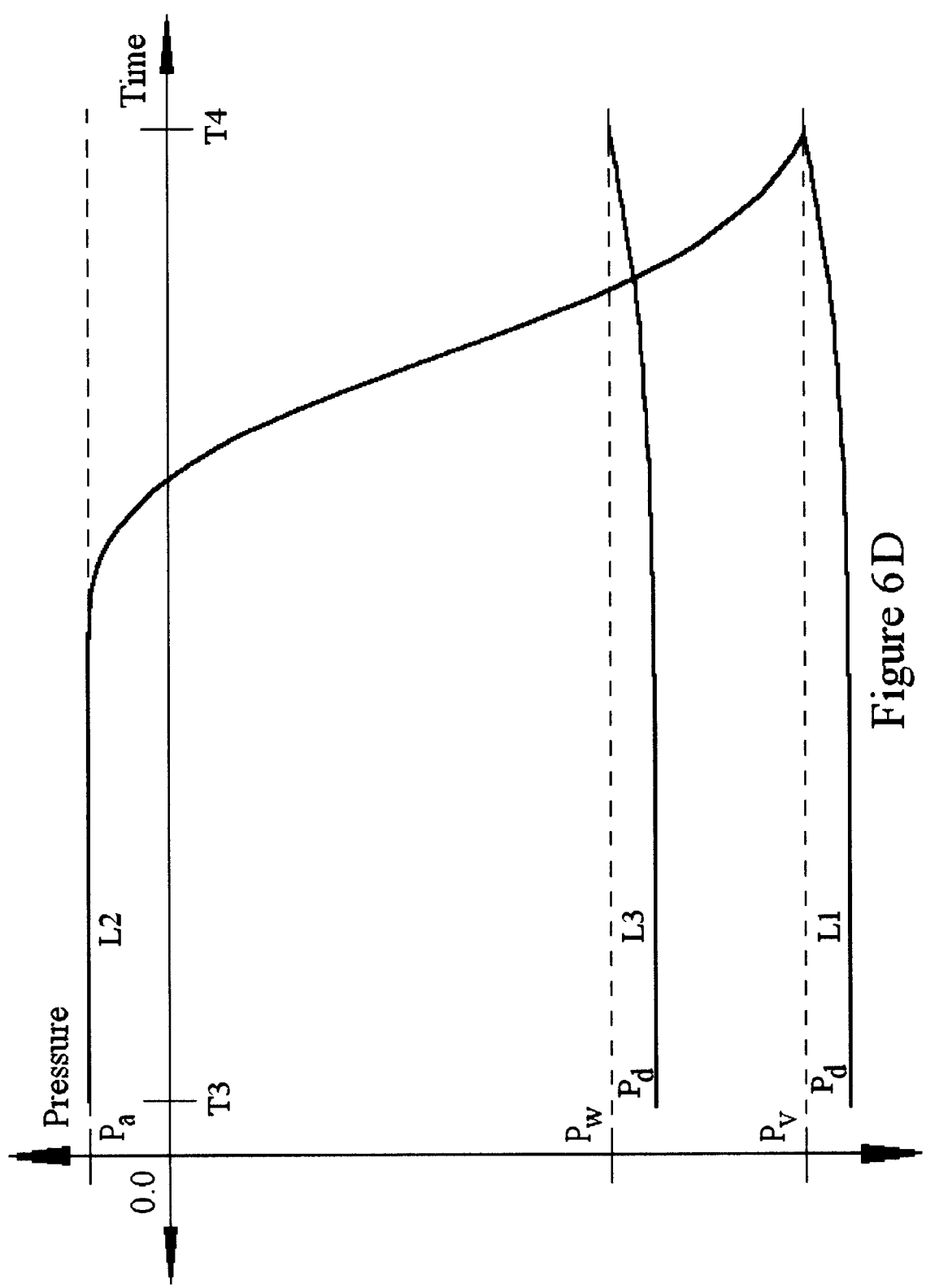
Figure 6E:
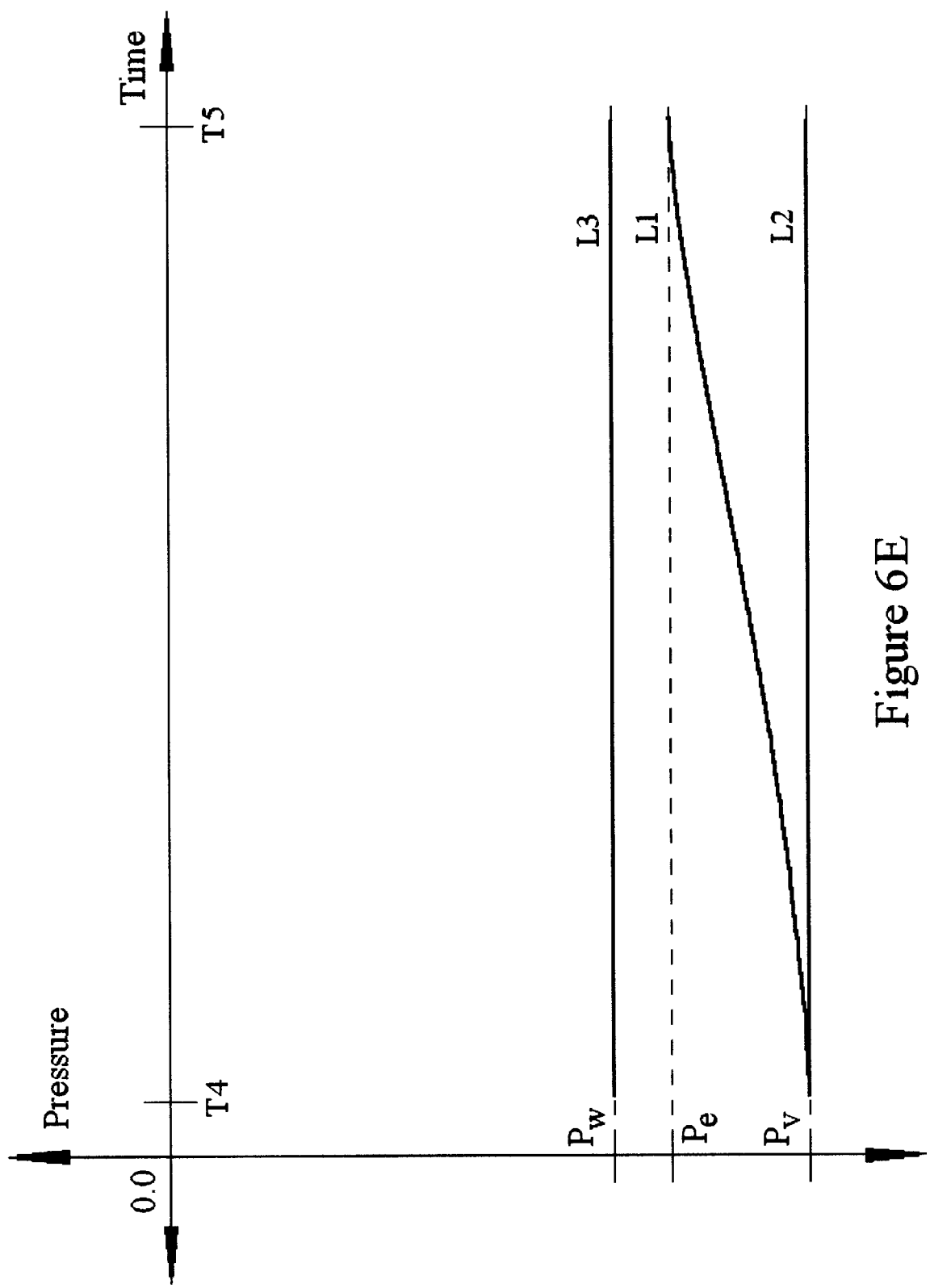
Figure 6F:
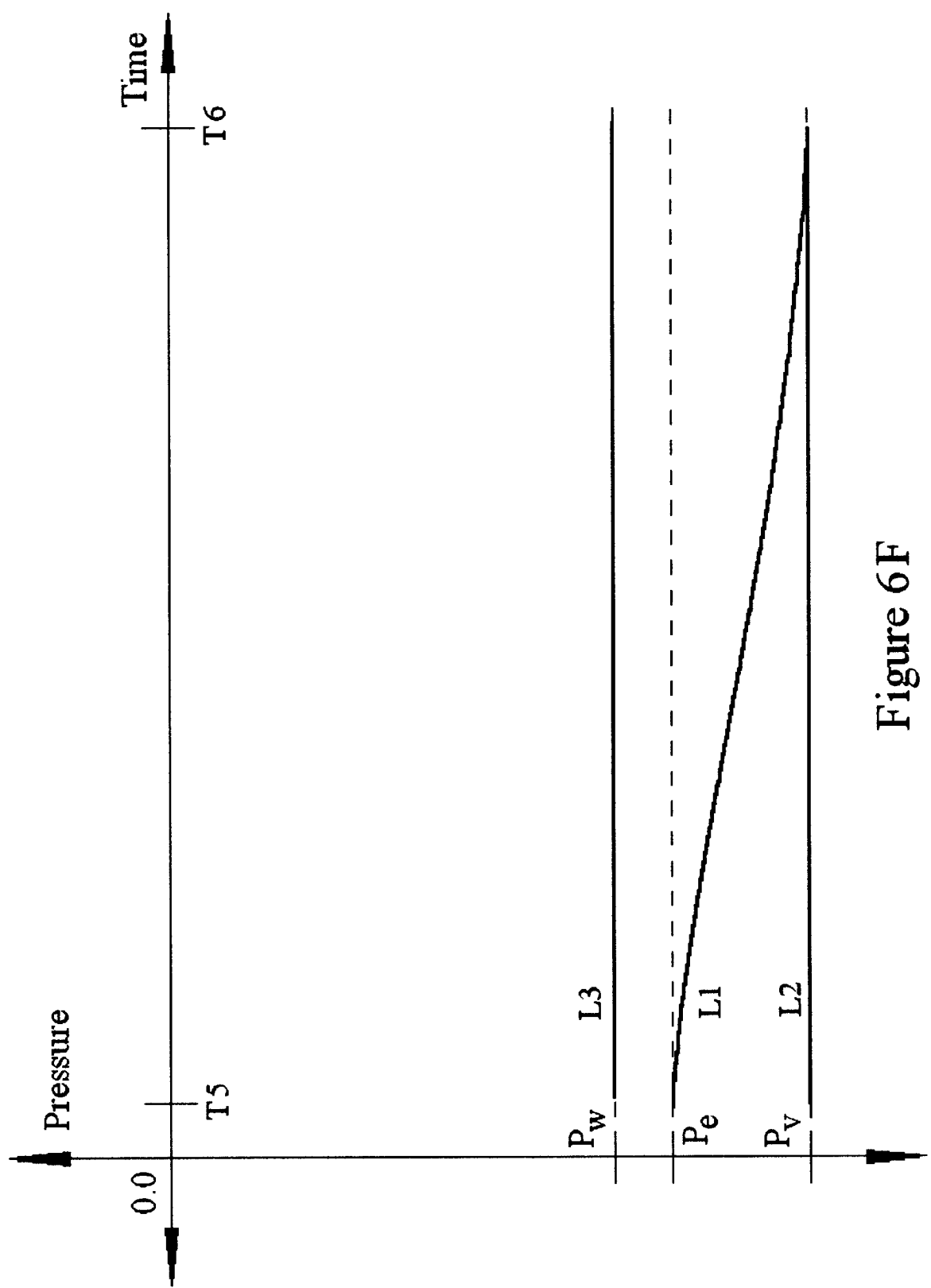

The complete operation of ACBES is described by the eight steps listed below. Pressure curves and parameters are provided in FIGS. 6–6H to assist in the explanation of the exemplary operational characteristics of each phase. This description represents a single application of the device to a patient. In practice, the device may be used repeatedly during the day for over two weeks.

The control box 20 (FIG. 3A) would generally include a pneumatic pump, which design may be from a number of off-the-shelf products currently on the market, the particular design for the particular application varying depending on the time dependent pressure variations required for device operation. A physician would like the option of adjusting the pressure levels during application via keyboard input, software protocols, or the like.

By visual inspection of the local tissue, the physician would generally be able to discern the need for increased or decreased pressure for extraction or actuation. All parameters given here are based upon the average values collected for the actual application of a medicinal leech.

The line 22 utilized interface the AHM 21 with the control box 20 in the present embodiment would comprise a three tube strand, which would interface with lines 1–3 (L1, L2, and L3, controlling the vacuum line, piston drive line, and medication supply lines, respectively, all of which would be initiated, monitored, and controlled at the control box.

In use, the desired medication could be mixed, or, if desired, dispensed separately via fluid pump controlled by the control box 20, running through line L3; air pressure would be created by an air pump controlled by control box 20 for controlling the movement of piston ring 33 via line L2, and suction would be provided via air pump secured to the vacuum line L1, with any blood or other fluid retrieved into suction line being drained into a container, as is customary in the medical arts.

In preparation, a sterile AHM is chosen, lines L1, L2, and L3 are attached, and the control box initiated and programmed, as desired.

A. Device Attachment (Time: 0 to T1 as is shown in Graph 6A)

Figure 3C:
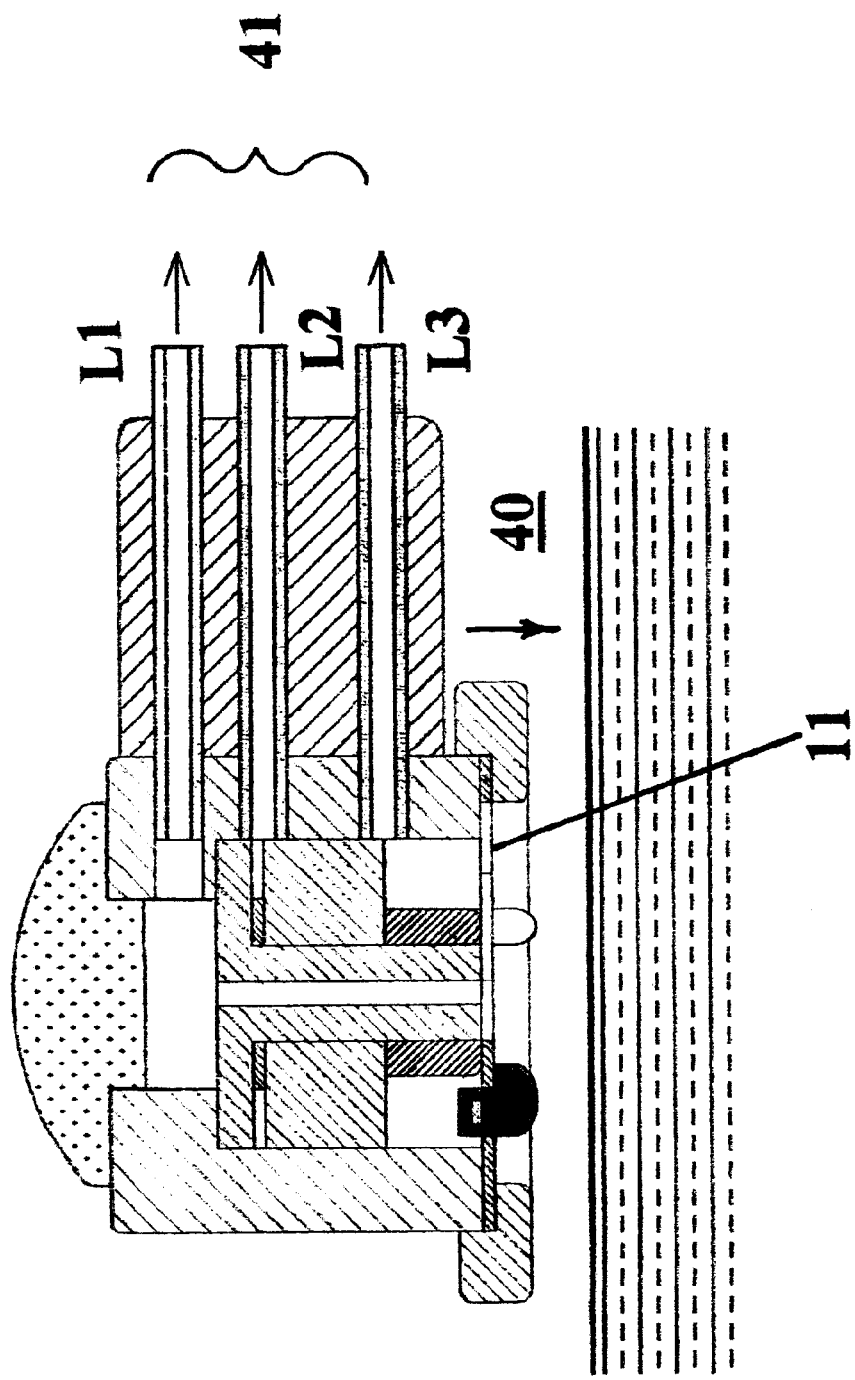
FIGS. 3C–3F illustrate a the application of the preferred embodiment of the AHM to a patient, and various steps in extracting blood from the tissue of a patient, utilizing the invention of FIGS. 1A and 1B.

Referring to FIG. 3C, the AHM 1 is placed 41 at the desired attachment site on the patient 26. The pressure 41 is reduced in all three lines L1, L2, L3 to a preset value of Pv. This is sufficient to maintain attachment and induce blood flow during Phase E, discussed infra. The leech's pressure drop has been measured at 1/10 atmospheres. This will be the presumed value for Pv although for exceptional cases, the pump should be able to deliver a vacuum of 0.3 atm below local air pressure.

Pv=0.3 atm (maximum) Below air pressure.

T1=1 minute.

B. Washing (Time: T1 to T2, as shown in Graph 6B)

Figure 3D:
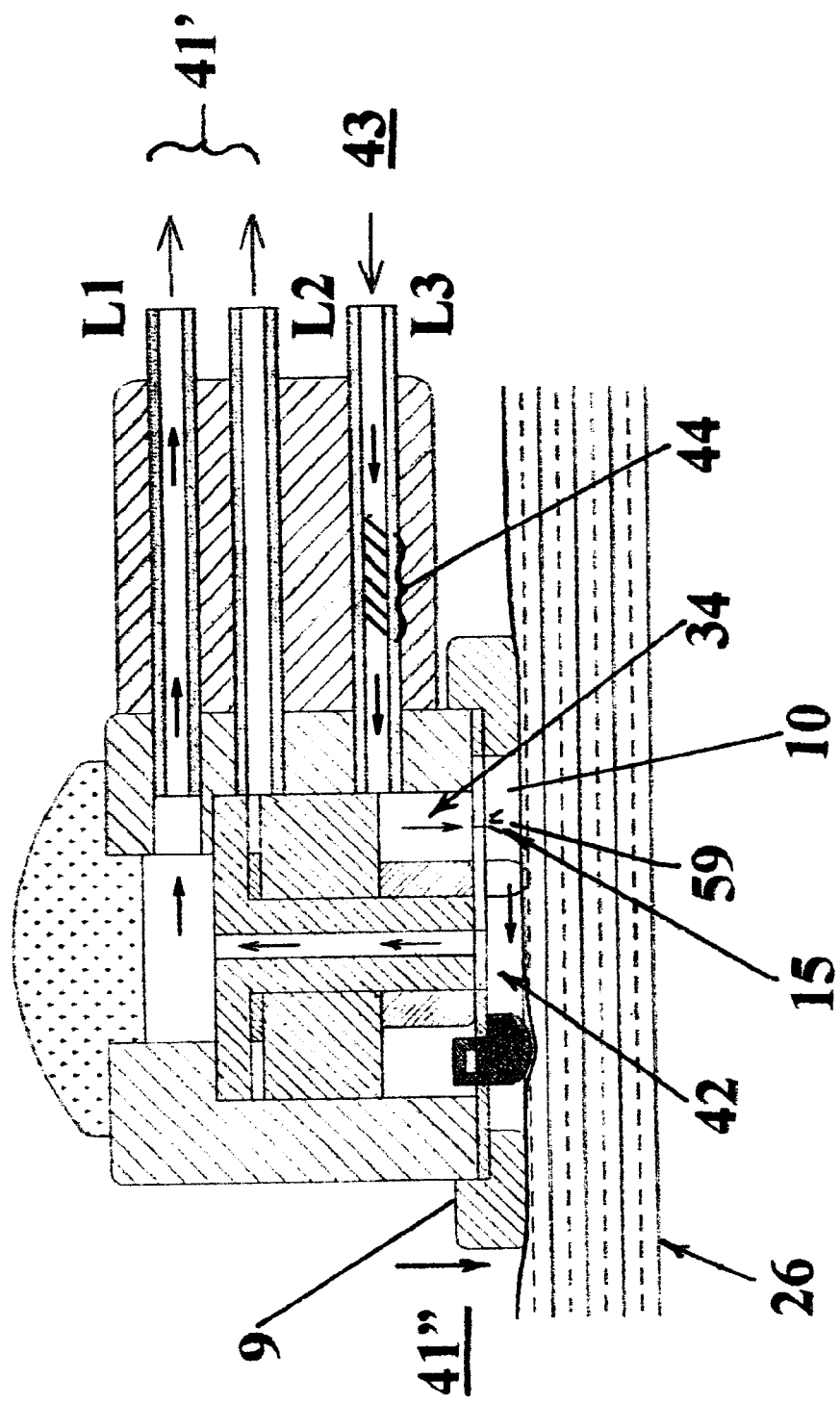

Continuing with FIGS. 3C and 3D, once the device is attached, the suction 41' from line L1 draws 41" the base of the unit against the skin of the patient 26, as the lip 9 at the base forms a seal, allowing the lower pressure 42 formed within the extraction chamber 10 to engage and pull the skin of the patient 26 against and within the chamber in response to the lowered pressure therein.

Next medication including an anticoagulant solution is supplied via line L3. The solution 44 is forced to flow through the line L3 via pressure 43, and on through medication chamber 34, where it passes through medication application orifices 15 formed in diaphragm 11, finally emanating from the opening of the orifice in the extraction chamber as a spray 59 upon the skin situated in the vicinity of the extraction chamber.

Thus, a fluid circuit is achieved and the anticoagulant solution, which may also include, for example, anesthetic, antihistamine, anticoagulant, antibiotic, or the like, making same present at the extraction site. Flow occurs by raising the pressure in line L3 from Pv to Pw. The value of Pw depends on the viscosity of the solution, thus Pw would vary depending on the chosen anticoagulant. The difference between Pv and Pw is likely to be one third of Pv.

Pv−Pw=Pv/3.

T2=1 minute.

C. Jaw Actuation Step 1 (Time: T2 to T3, as shown in Graph 6C)

The leech scratches the skin until it is able to achieve blood flow from its host. In this manner, only the surface venous capillaries are effected. Thus, the ACBES device is actuated by a positive fluid pressure that flows through L2, through compressing chamber 19, forcing piston ring 33 against beam 35, providing tension. The beam 35 engages 51 each jaw plate, from movement 49 exerted by piston ring 33, which is actuated via pressure 48 from L2, causing beam 35 to move 50 toward diaphragm, the force translated to beam against each jaw plate, pivoting 52 or rocking same to engage and scratch against the skin of the patient. The actuation pressure (Pa) in line L2 must push the piston against the friction of the diaphragm or the j-beams (when employed), and the resistance of the skin. The fabrication processes chosen to produce the device are intended to minimize these forces. Currently, Pa is estimated at 0.7 atmospheres above the vacuum pressure (Pv).

With the downward movement 49 of the piston ring, the ring, in this embodiment of the invention, blocks 54 medication from being dispensed by L3, which medication 44 is allowed once again (referring to FIG. 3F) to pass into medication chamber 34, and applied 59 upon the skin upon the lifting 58 piston ring, which may be effected by providing a vacuum 57 in L2, where necessary, although it is believed that the elastic properties of the diaphragm 11 would likely force the beam and piston to lift 58, without the necessity of a vacuum; with the diaphragm 11 (or j-beams, when employed), returning to its original position with the pressure relieved from L2, the jaw plates, which communicate with the diaphragm (or j-beams, where employed), once again rock or pivot 60 to their original position, again contacting, scratching, and/or serrating the skin; it is noted that the vacuum continues in L1, with the low pressure area in the extraction chamber 10 continuing to engage the skin of the patient.

Ideally, to ensure the maintenance of adhesion during actuation and to compensate for the motion of the piston, the pressure in lines L1 and L3 are reduced by Pd. This minimal pressure drop is anticipated to be, for example, less than one tenth the vacuum pressure.

Pa=0.7 atm (2 atm maximum).

Pd<Pv/10.

T3=5 seconds.

D. Jaw Actuation Step 2 (Time: T3 to T4, as shown in Graph 6D)

As discussed above and illustrated in FIG. 3F, the pressure in L2 is reduced to Pv, allowing the diaphragm (or j-beams, when employed), constructed of elastic material, to return to its original position, driving the beam and piston upwards, and allowing the jaw to return to its original position. This completes one oscillation in the jaw motion. Depending on the jaw teeth size, the local skin thickness and the severity of the blockage, steps "C" and "D" above are repeated until a sufficient wound is produced.

Figure 3E:
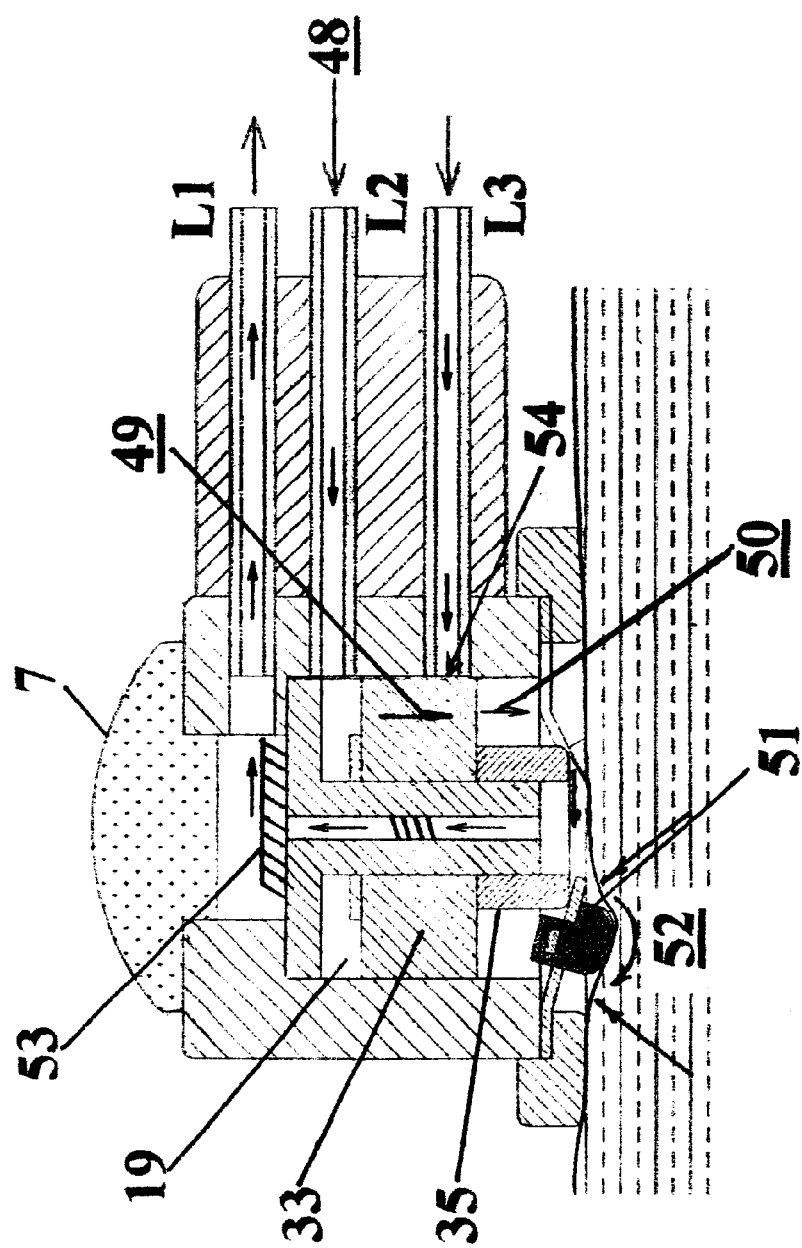
Figure 3F:
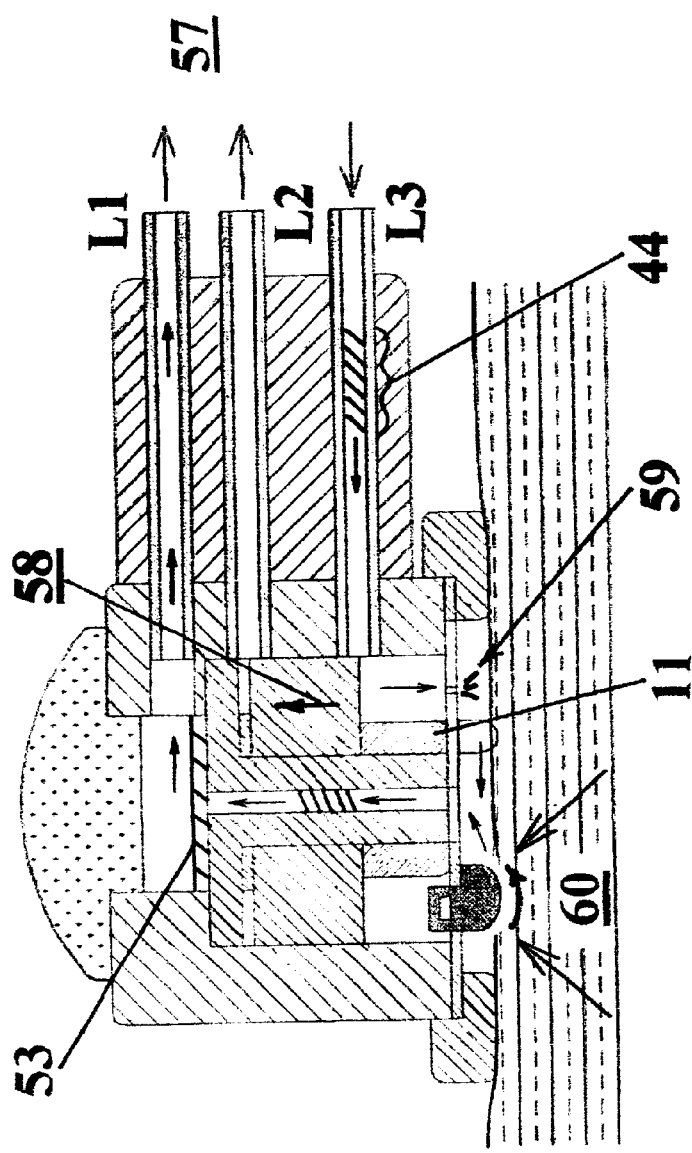

At this point, the decision to continue actuation or switch to the extraction phase is made based upon visual observation through dome 7 for blood flow 53 (as shown in FIG. 3E) and extraction via suction from L1, or the sensed pressure change in line L1, which could be monitored via control box.

T4=5 seconds.

E. Blood Extraction (Time: T4 to T5, shown in Graph 6E)

The previous two steps are repeated until blood flow is sensed. This will appear most significantly as a reduction in the vacuum of line L1. The extraction pressure increase (Pe) is dependent on the jaw incision and the severity of the wound. In non-obstructed tissue, the blood pressure is above local air pressure. The sudden release of a relatively large volume of blood at normal pressure will cause the device to automatically detach. Obstructed tissue will gradually release blood at an extraction pressure of Pe. Experience with the medicinal leech has shown this pressure to be about one fifth the vacuum pressure. However, the pump must be able to sense small pressure changes as low as 0.005 atm and recover from larger pressure changes of up to 80% of the vacuum pressure.

Once a wound is produced which reaches viable capillaries, the time to a sensible pressure change will be seconds. Thus, step E functions in conjunction with steps C and D. The physician is assisted in determining the initiation of blood flow by viewing the exiting fluid through the transparent dome 7 at the top the each device.

Pe=0.02 atm.

T5=10 seconds.

F. Vacuum Restoration (Time: T5 to T6 as shown in Graph 6F)

For some cases, the restoration of the vacuum pressure is not necessary. However, for the most critical cases, maintaining an acceptable extraction rate will require a higher vacuum. For the full range of possible applications, it is necessary to assume the worst case scenario and provide for this vacuum recovery function.

Eventually, ACBES will cause the tissue to recover its full flow rate and thus the blood pressure will invariably increase. As this occurs, the attending physician will note a high extraction rate for the given vacuum pressure and thus shutdown the pump since the goal of restored circulation has been reached.

T6<1 minute (Depends on pump design.)

Figure 6G:
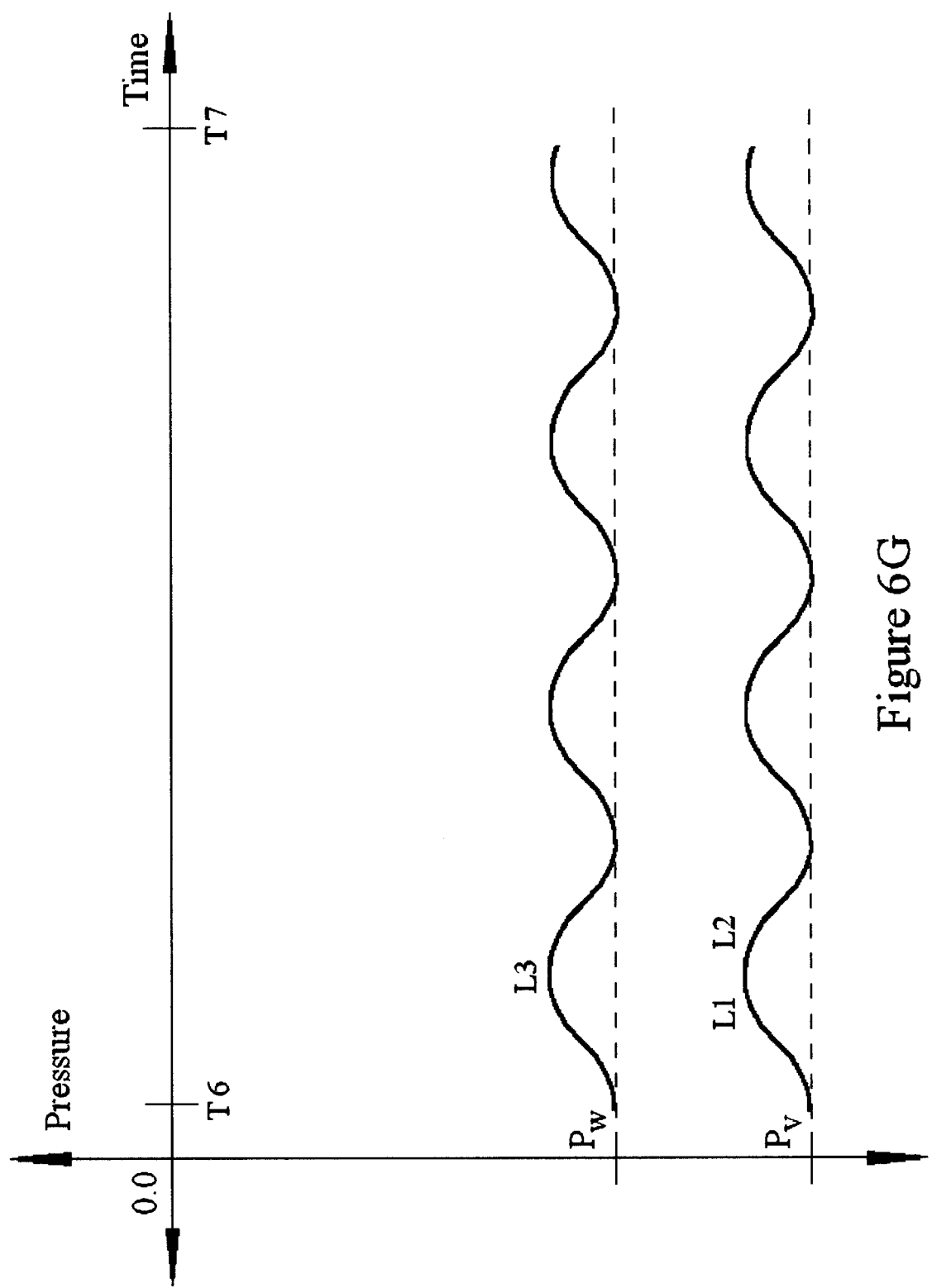
Figure 6H:
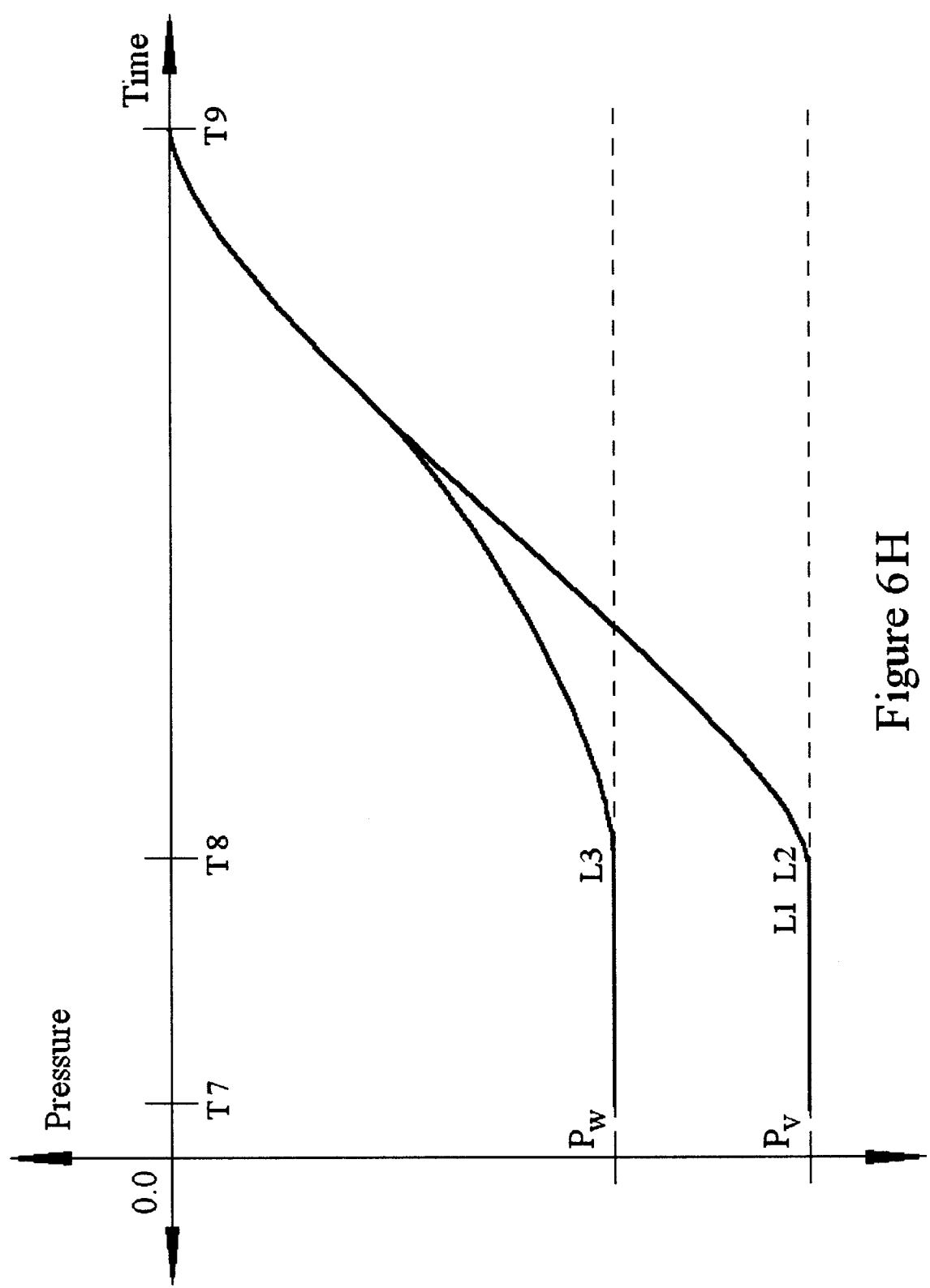
Figure 7:
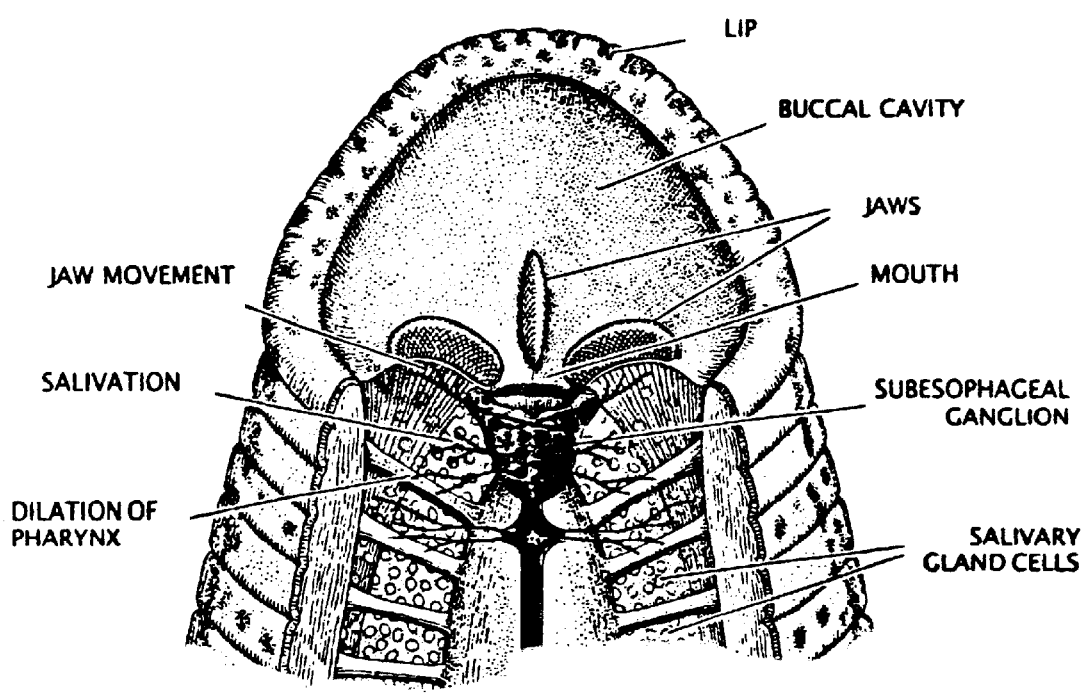
FIG. 7 is a partially cutaway, isometric view of the typical medicinal leech, Hirudo Medicinalis.

G. Drinking (Time: T6 to T7, as shown in FIG. 6G)

Assuming the tissue circulation is not immediately restored, the device further mimics the leech by extracting blood in a "drinking" fashion. The leech pulsates the opening and closing of its throat at a frequency of about one fourth hertz (four times per second) while maintaining a vacuum. This allows the ingestion of the blood. Also, a little know phenomena occurs. As the pressure is decreased over the tissue, a sponge-like effect induces a back flow of liquid from the device cavity (or leech's mouth) into the tissue causing the absorption of the anticoagulant. This helps to clear the capillary blockage.

During the drinking phase, the blood flow may be reduced due to excessive blockage of the wound site. For this case, the pump must stop the pressure oscillation and return to the base pressures for each line (L1 and L2 at Pv and L3 at Pw). Then the jaws are re-actuated to either reopen or deepen the wound and the process continues to the drinking phase again. Should circulation be sufficiently restored to the tissue, the extraction process may be stopped.

Oscillation Pressure Amplitude=0.02 atm.

Oscillation Frequency=0.25 Hertz

T7=Until re-actuated or shut down is decided. (From 30 minutes to 8 hours.)

H. Shutdown (Time: T7 to T8 and T9, as shown in Graph H)

Release of the device from a patient can be performed in a controlled manner. The oscillation of step G is ended and the line pressures are returned to their respective base pressures. Then the vacuum pressure of each line is slowly restored to normal air pressure. As the vacuum is reduced, the device will detach due to its own weight. As an option for shutdown, the fluid in line L3 can be switched to a coagulant and antiseptic. This will close the wound at the surface and thus leave a sealed and sterile wound site. This is an exceptional advantage over the medicinal leech which leaves an open bleeding wound that becomes infected for about 20% of the case applications.

T8=10 seconds.

T9=30 seconds.

The above pressures, time intervals, and other figures are illustrative examples only, and not to be taken in a literal context; it is anticipated that these figures can fluctuate considerably, depending upon the application, environment, patient, wound, medication, device design, and other criteria.

ACBES can be operated by a drive pump which delivers a time varied pressure to each of the three fluid lines L1, L2, L3. Since the pressure differences are on the order of one atmosphere and the volumetric flow rates are on the order of one cubic centimeter per minute, manufacture of an electronically controlled drive pump is within the limits of current technology. The pump required for ACBES is of the same sophistication as the drive pump produced by Camp for the therapeutic sleeve marketed by Healthtronix Medical Equipment Incorporated.

Summary of Characteristics of Preferred Embodiment

On top of the AHM is the transparent dome to magnify the extraction channel for verification of blood flow. The skirt along the bottom is an elastic "lip" to ensure a pressure seal without damage to the tissue.

An operational hose is attached to the right extension shown in the top sketch. This hose has three channels: the top channel extracts the blood, the center channel operates the piston for jaw actuation, and the bottom channel injects a special solution it assist with blood extraction. The piston cavity (or compression chamber) is pressurized to move the piston downward and actuate the jaw pieces via the beam. The pressure is released and the elastic stress of the diaphragm to the jaw mount return the piston to its original location. This process is repeated to form an incision in the skin like the jaw action of a leech.

The three jaw pieces mounted in the jaw plate form the means of incision. The "teeth" details of the jaws are shown but best viewed in the jaw diagram, discussed infra.

The piston, the piston guide and the central drain line must be machined to form a pressure seal. The transparent dome window may be formed from glass or plastic. Its shape magnifies the interior to yield a "dot" to indicate blood flow.

The thickness of the plate and the width of the beam varies depending on the application. The elastic nature of the metal allows deformation and return of the any jaw support member which could support the jaws. The jaw plates may be mounted via pivotal connection to a mount ring sealed to the housing to hold the jaw plate to the main cylinder.

Figure 4:
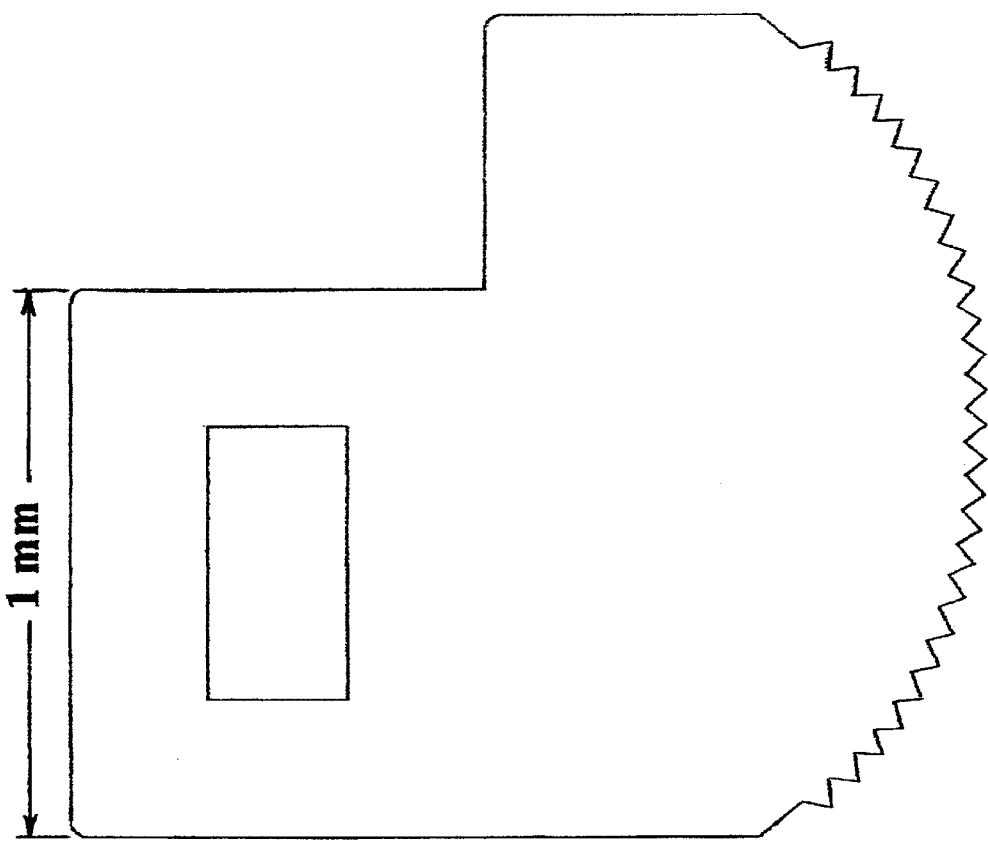
FIG. 4 illustrates a side view of the preferred, exemplary embodiment of the sawtooth jaw blade of the invention of FIGS. 1A and 1B.

FIG. 4 illustrates a side view of the Sawtooth Jaw. The thickness may be, for example, about 0.1 mm. The jaw may be supported by direct connection with the membrane, or may supported via clip securing the jaw to a jaw plate, which could incorporate an adhesive to hold the jaw in place. An adhesive may further be used to hold the clip in place. The exemplary embodiment of the sawtooth design has 25 triangular teeth with a width of 60 um and a height of about 40 um. Jaw curvature, tooth shape and jaw thickness vary depending on the patient application site, thus a collection of jaw designs will be added to the current designs.

Figure 5:
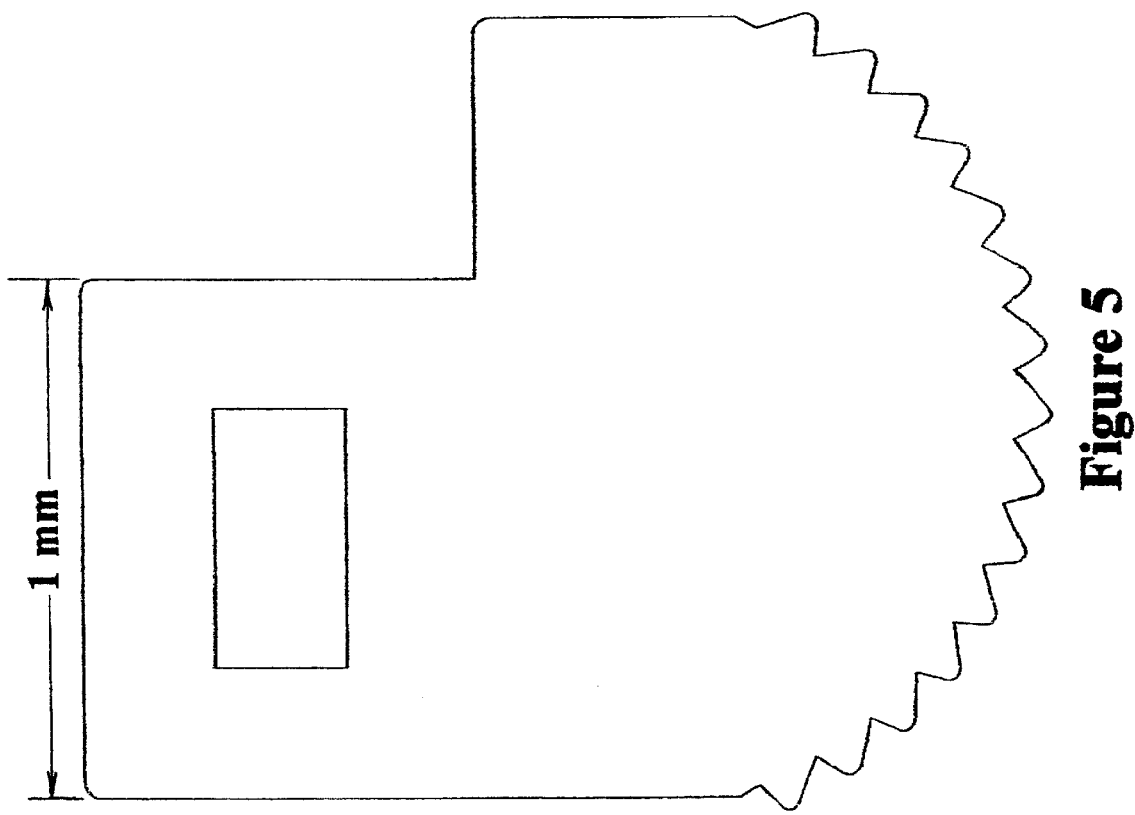
FIG. 5 illustrates a side view of an alternative jaw blade of FIG. 4, illustrating a directional jaw blade and tooth configuration.

FIG. 5 illustrates a directional jaw configuration, which could provide an alternative incision means, depending on the thickness of the skin. FIG. 5A provides an enlarged view of a directional jaw tooth. The teeth may be of varying sizes and shapes. For example, they could be triangular like a saw and larger for cutting thicker skin.

Exemplary Parts Descriptions

Piston Chamber/Cylinder

Milled from stainless steel.

Tolerance on inner wall must match the Piston tolerance.

Hose Attachment for Lines L1, L2, L3

Compression molded plastic.

The needles are sealed to the Hose Attachment and the Hose Attachment is sealed to the Main Cylinder by an adhesive chosen by the Hose Attachment manufacturer.

View Dome

Compression Molded from transparent plastic.

The View Dome allows the user to see the initiation of blood flow and to verify the flow level during extended operation.

Piston Guide or Suction Conduit

Fabrication method has not been determined.

The tolerance on the shaft outer surface must match the tolerance on the piston rings inner surface. A Piston Guide may be sealed to the piston ring to prevent leakage between the piston drive pressure and the blood extraction pressure.

Piston Ring

Fabrication method has not been determined

High tolerance on the inner and outer surfaces. The tolerance must match the Main Cylinder and Piston Guide. The piston must form a dynamic pressure seal for actuation.

Piston Stop

Electro-molded with low tolerance on the outer edge.

This part acts as a "filler" between the Piston and Piston Guide. It prevents the Piston from closing the gap forming the compression chamber, with receives the fluid pressure from the second line for actuation.

Piston Pusher or Beam

Fabrication method has not been determined.

Low tolerance on the outer edge. The jaw plate beams are pushed by this part. It allows that fabrication of a simple cylinder for the piston instead of the previously proposed design which was complicated and expensive to construct.

Jaw Plates

Electro-molded.

Low tolerance is acceptable on all sides except for the slits that hold the Jaws. These openings must tightly fit the Jaw width and thickness. The thickness of this part depends on the required spring recoil.

Jaw Plate Mount Ring

Compression molded plastic.

A Mount Ring may be adhered to the Main to hold the Jaw Plate in place against the force of the piston.

Jaw

The mechanical jaw shape is intended to follow the curvature of the leech jaw. The jaw is 1.5 millimeters across. The mechanical jaw's depth is artificially extended to compensate for the distance from the jaw mount to the outer lip. The extension will yield the correct cutting depth during operation. There are several tooth shapes that will be employed depending on the physiological attachment location.

The most versatile profile is the triangular shape. The jaw is flat at the center and curved towards the edges. There are 25 teeth-like ridge points along the edge that act as a saw for opening a wound. The teeth shape is triangular with a base of 60 um and a height of 40 um. A modified triangular design allows a directional cut with reduced resistance during retraction. This jaw must be thinner than the sawtooth jaw. It is designed for the tougher skin that covers fingers and toes. A thickness of 100 um is preferred. As indicated, the jaw may be supported directly by the diaphragm, in the case of a diaphragm made of an elastic material, such as silicone or the like, or, in the case of a non-elastic material such as metal, the jaws may be supported by flexible j-beams, and secured to a jaw mount by a clip. This clip shape shown before assumes the jaw will be adhered to the jaw plate via adhesive or the like.

All units are in millimeters.

All fillets are preferred in proportion to that shown but subject to change as fabrication requires.

FABRICATION REFERENCES

Drive Pump (Controlled by Control Box)

A drive pump of the type needed to operate ACBES is manufactured by Camp of Jackson, Mich. The pumps are digitally controlled with feedback response for pressure adjustments. This range of time dependent pressure variations as shown in the operation section, can be easily supplied by these pumps. They are often referred to as "multi-chambered digital pumps".

Connection Hose

The tubing which connects the extraction device (AHM and others) to the pump is produced by Kloehn Micro Syringes of Los Vegas. They manufacture special use syringes and stainless steel tubing the size of hypodermic needles.

Extraction Device (AHM)

The main housing of the AHM, the piston, the piston guide, the piston stop and jaw pusher may be produced by precision machining like that employed by the National Jet Company of Lavale, Md. They make and use micro milling machines and drills. Their equipment can produce the mentioned parts by turning steel mini-ingots.

The jaw plate, jaw clip, and jaw may be fabricated by use of electro mold forming (EMF) as used by Dynamics Research Corp. of Wilmington, Mass. This new (10 years old) process produces planar metal structures on the order of 100 um thick with feature resolution down to 5 um. These are precisely the characteristics needed to economically produce a mechanical leech jaw.

DRC can also produce the jaw mount ring, the transparent view cap, and the hose connection lure by standard compression molding. (Note: The plastic piece that hold a needle to a syringe is called a "lure" within the industry.)

The tubular inserts that connect the main housing to the connection hose by way of the lure may be produced by Kloehn.

Assembling the device is obvious with the condition that the view cap, the jaw plate mounting ring and the hose connection lure may all be sealed by an adhesive commonly used for syringe manufacture, as is supplied by Kloehn. Also, the jaw clip, if employed which holds the jaw to the jaw plate may be sealed with that same adhesive.

FIGS. 9A–9F illustrate a similar view of the invention of the preferred embodiment, with only minor mechanical differences shown therein.

As shown in FIG. 9A, the device similar to that illustrated in the device of FIGS. 3C–3F, but illustrating a flat 7' instead of the domed view portal earlier shown, and a piston P which engages the diaphragm directly to rock or pivot the jaw plates, which are shown supported by the diaphragm itself (which is fabricated of flexible material).

FIG. 9B illustrates placement of the alternative embodiment of the AHM upon the tissue T of a patient and the initiation of a suction through all lines, including through line L1, to initiate a seal of the skin within the extraction chamber C, drawing the skin into contact with the jaw plates.

Figure 9C:
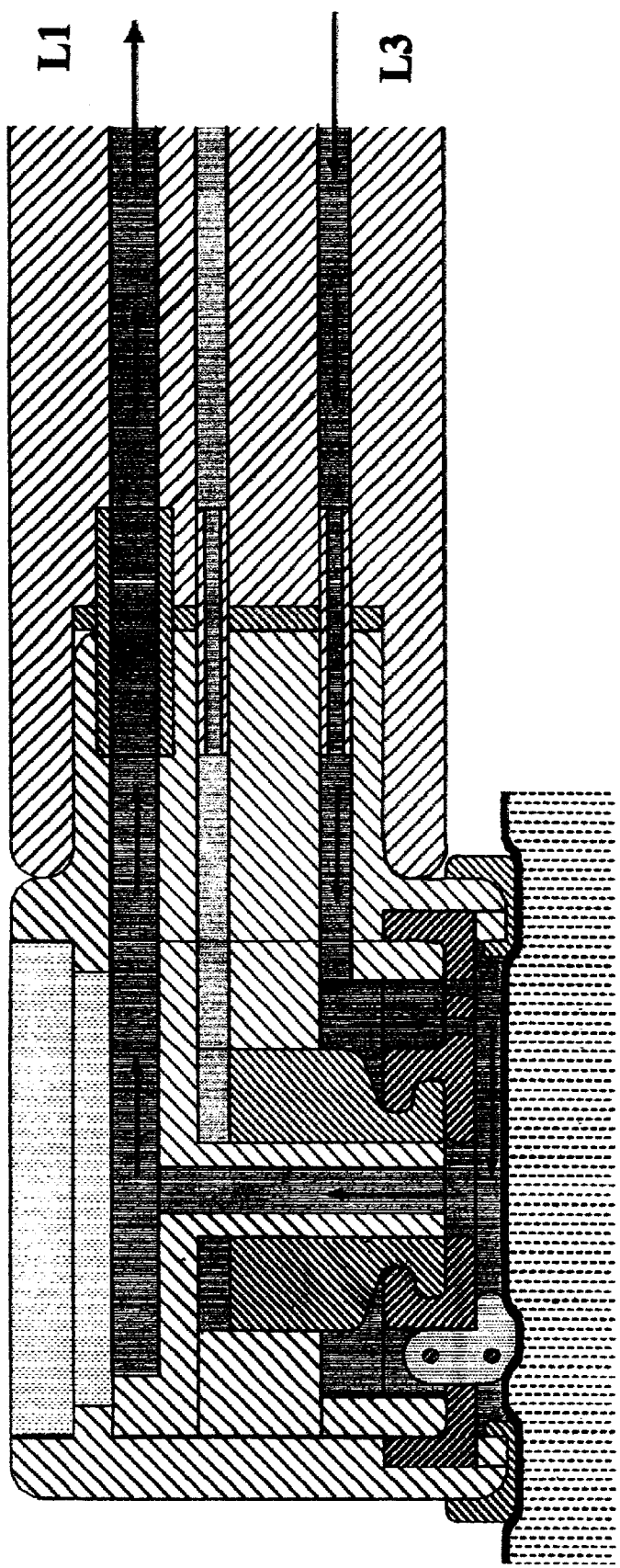

FIG. 9C illustrates the washing phase of the alternative embodiment, which, like the principle embodiment, comprises continued suction from line L1, drawing suction from the extraction chamber, with the providing of a medicinal fluid via L3, through diaphragm, "washing" the tissue to be incised, and removing the fluid thereafter.

Figure 9D:
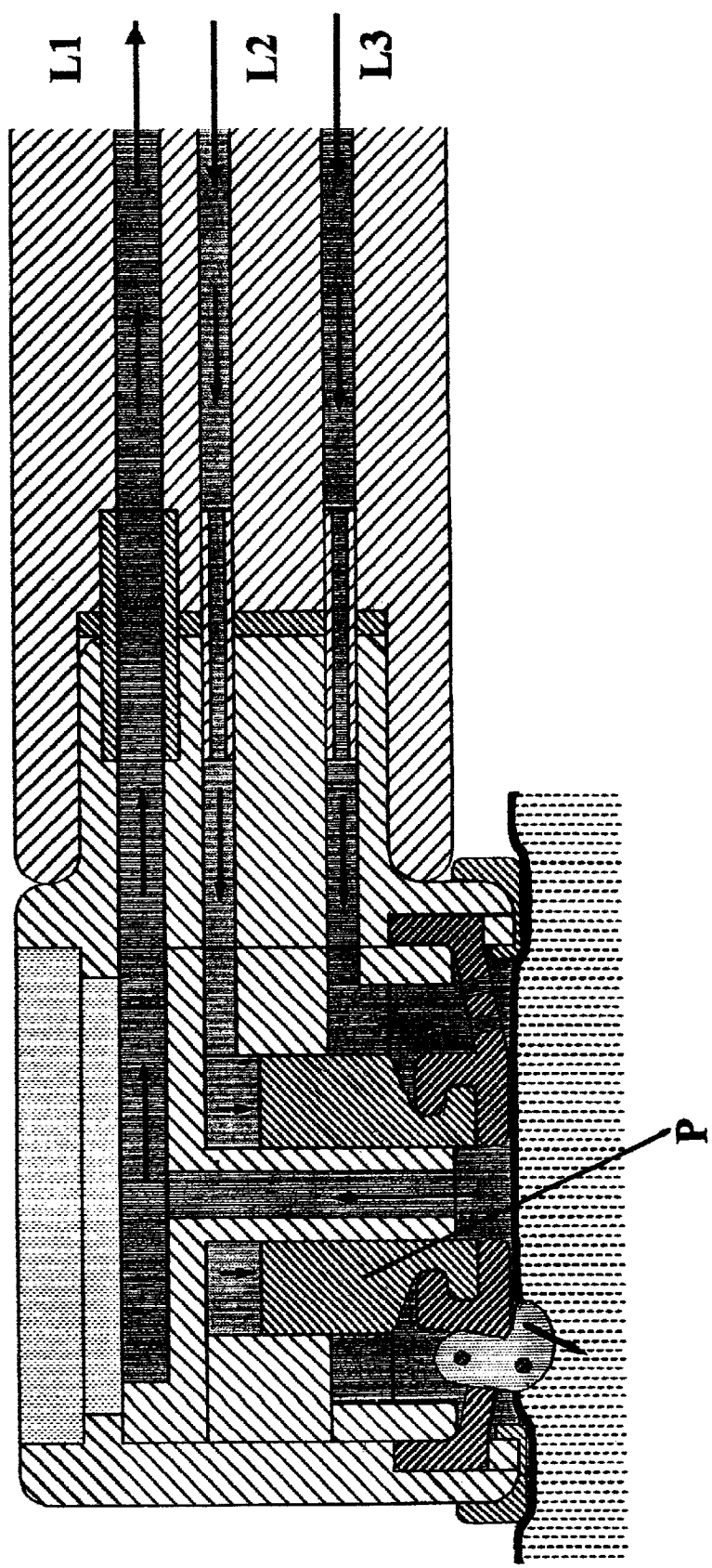

FIG. 9D illustrates the application of positive fluid pressure to line L2, forcing piston P downward, forcing the diaphragm against the skin, while rocking the jaw plates outward against the skin; suction continues via L1; note in this embodiment, line 13 is not blocked by the movement of the piston, and medicinal fluid may continue to be applied to the extraction chamber, as desired.

Figure 9E:
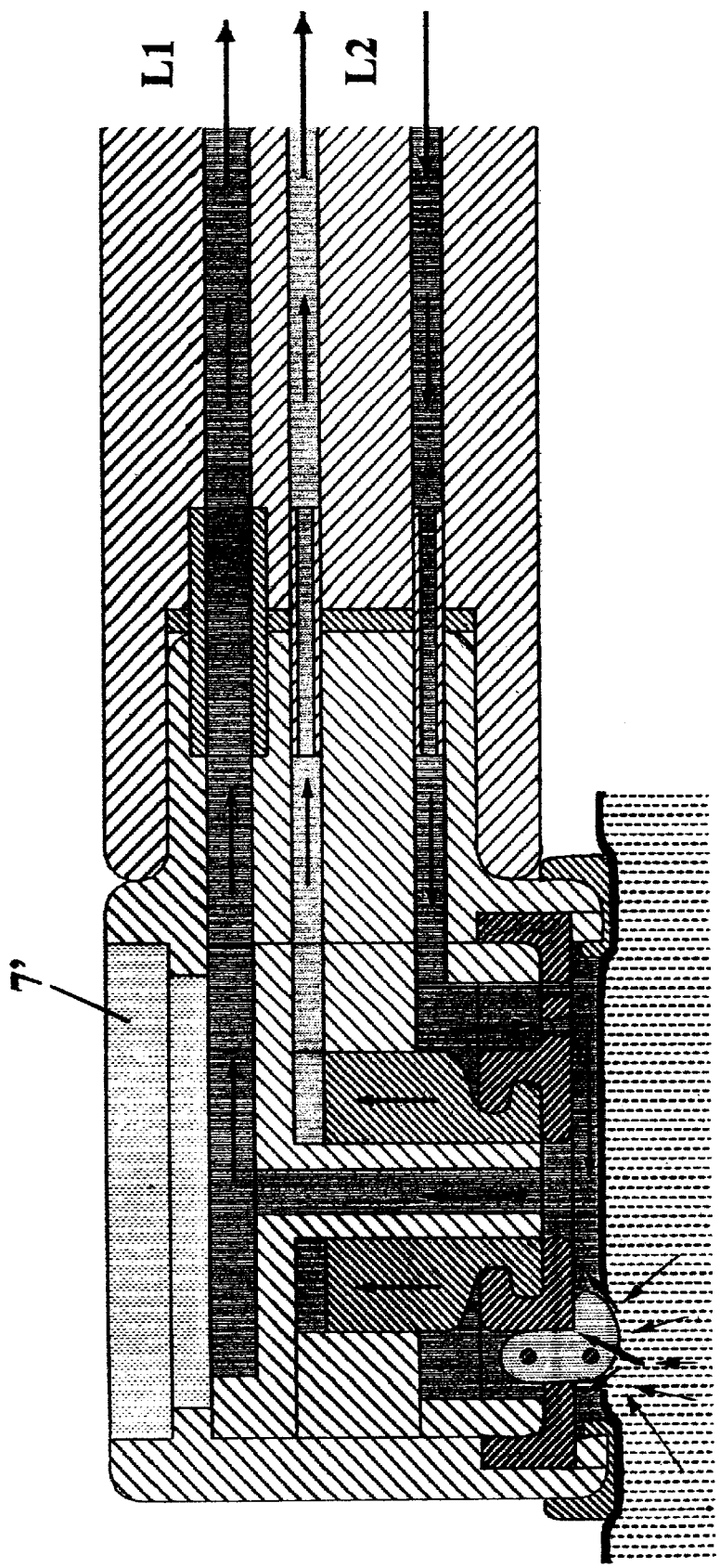

FIG. 9E illustrates the release of fluid pressure in line L2, allowing the diaphragm to force return to its previous position, forcing the piston up, and pivoting the jaw beams back to their original position, further incising the skin; upon the incision and bleeding of the skin, it will be extracted via suction from line L1, and viewable through flat 7' portal.

Figure 9F:
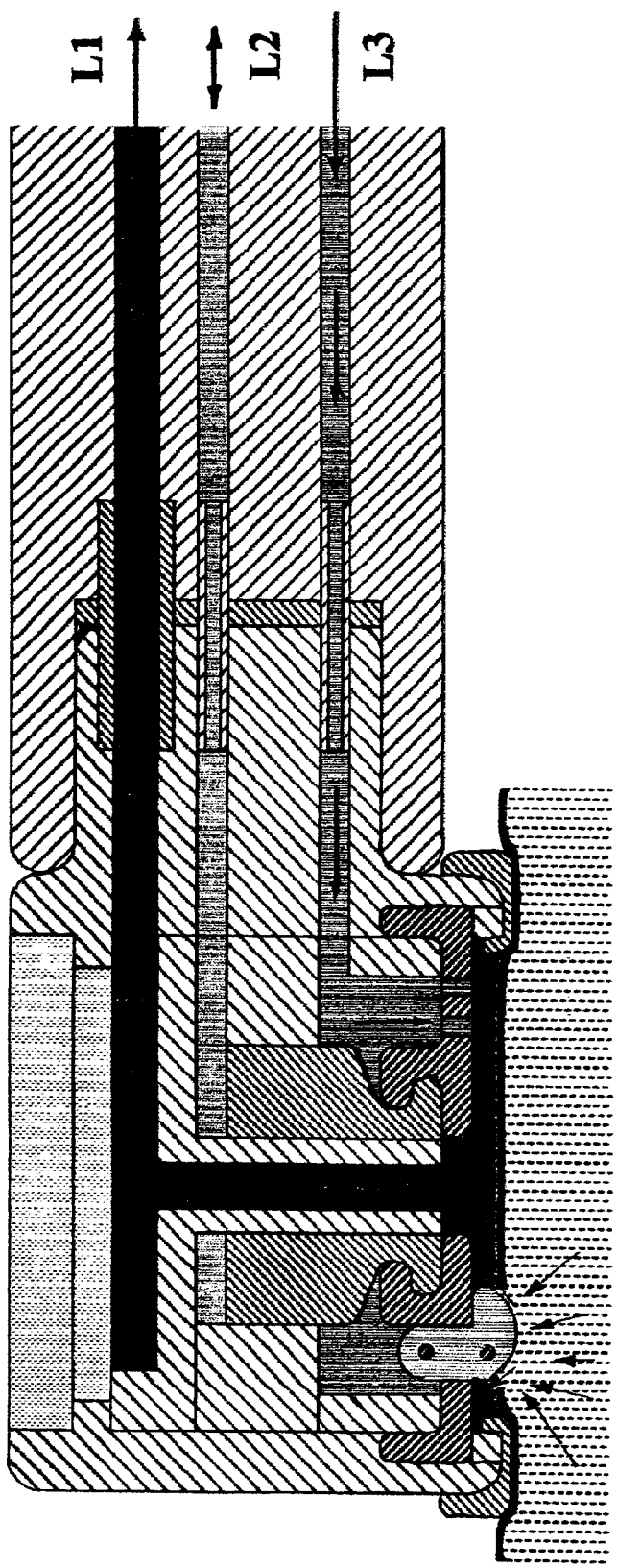

FIG. 9F illustrates the "drinking" phase of extraction, wherein the incision formed by the jaw plates bleeds, the blood is drawn via suction from Line L1, medication may be dispensed via line L3, and the jaw plates may continue to be rocked as desired via piston oscillating actuation from pressure via line L2.

Other Devices

Figure 10:
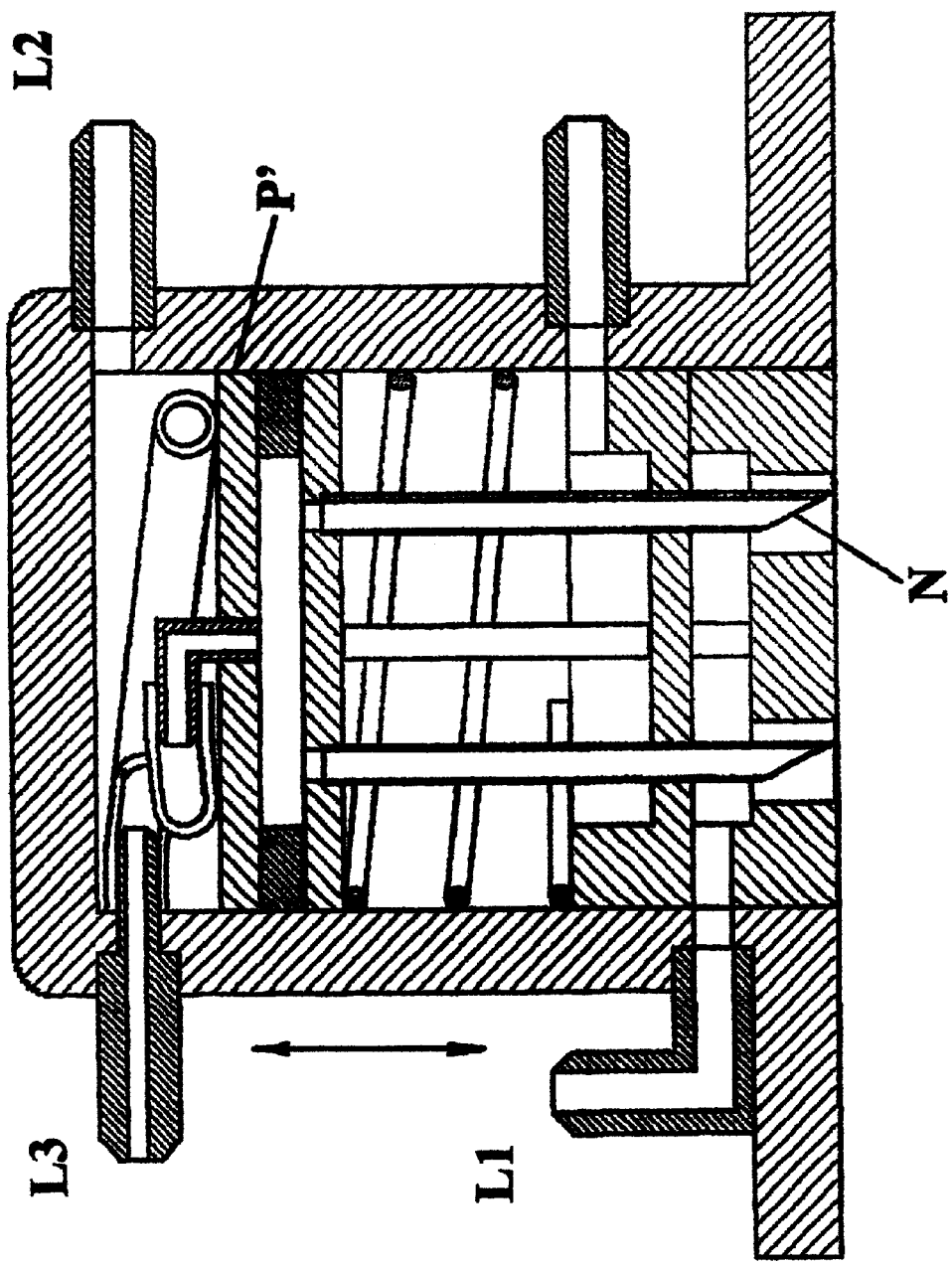
FIG. 10 illustrates a side, cross-sectional view of a third, multi-needled, alternative embodiment of the AHM of FIGS. 1A and 1B, utilizing a spring biased plunger design.

A third alternative embodiment of the present invention may be in the form of a needled extraction device, utilizing needles as the blood extraction means to extract blood or other fluid from tissue, as opposed to the incising blade-type devices discussed earlier. The first of such devices is shown in FIG. 10, teaching a multi-needled piston design configured to promote blood flow in severely injured tissues. This design can include more needles to cover a larger tissue area.

The basic operating principles of the device are similar. Line L1 provides suction for drawing blood from the tissue, while retaining the base in place against the skin of the patient. Line L2 provides fluid pressure to force the needles N downward via piston P' into the tissue, as desired, line L3 provides medication as desired. Also shown is a spring to provide upward bias, to urge the needles out of the tissue once pressure from L2 is relieved. The operational characteristics would fall generally in line with those disclosed in the preferred embodiment of the invention, above.

The needles may be formed from common materials such as stainless steel and medical grade plastics, where appropriate. The hypodermic needles (HDN) are standard sizes as produced by Kloehn (of Los Vegas) and Hamilton Company of Reno, Nev.

Figure 11:
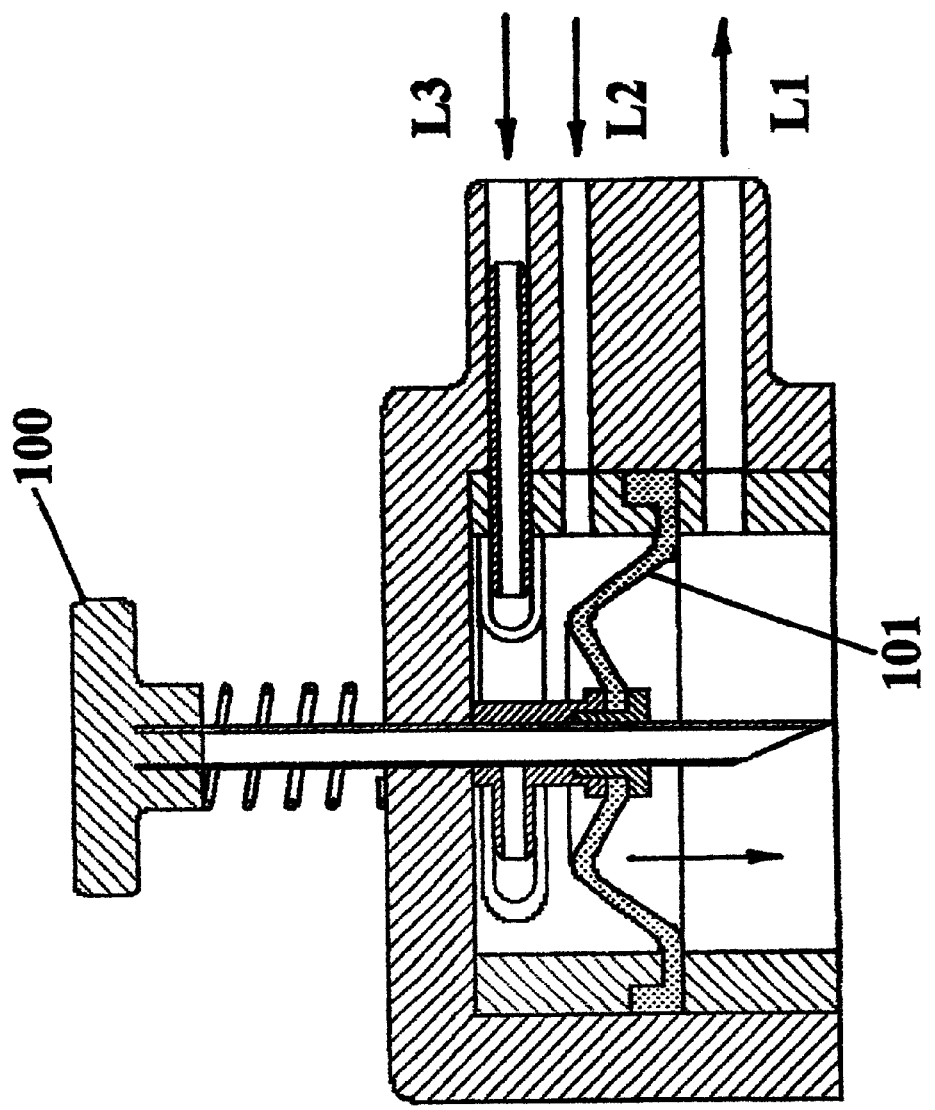
FIG. 11 illustrates a side, cross-sectional view of a fourth, single needle, alternative embodiment of the AHM of FIGS. 1A and 1B, utilizing a pneumatic having some similarities with that employed in the preferred embodiment of the invention.

FIG. 11 illustrates a simple single needle design, wherein the needle is held in an upward bias, and wherein the needle may be manually inserted into the skin by pressing a plunger 100, or alternatively by fluid pressure provided by line L2, urging the diaphragm 101 downward, along with the needle to which it is engaged. Medicinal fluid similar to those earlier discussed via L3 is through the needle; causing blood to flow into the extraction chamber, where it is collected via line L1 via suction. Upon relief of pressure from line L2, the spring urges the needle upward; bleeding continues and is suctioned via line L1; this may be prolonged through the application of anticoagulants, etc via line L3.

Figure 12A:
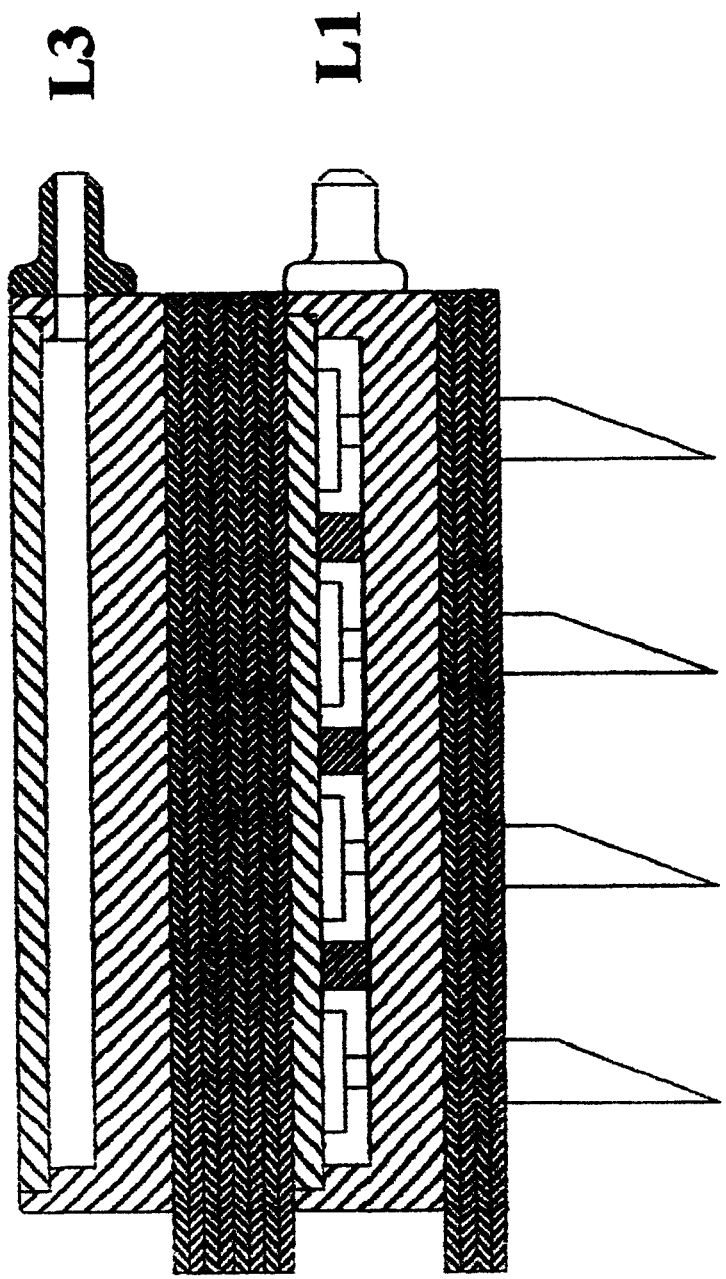
FIGS. 12A–12C provide side, partially cut-away, partially cross-sectional views of a fifth, multi-needle array version of the AHM of FIGS. 1A and 1B, illustrating the various positions of the components forming the device during operation.
Figure 12B:
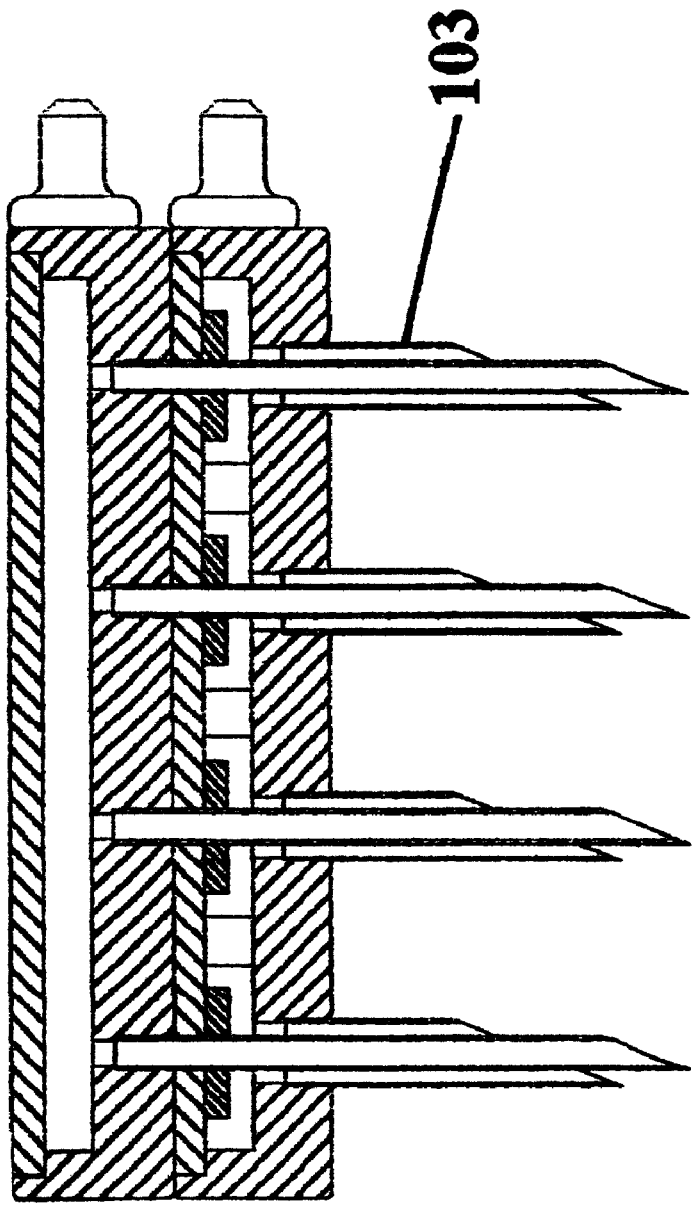
Figure 12C:
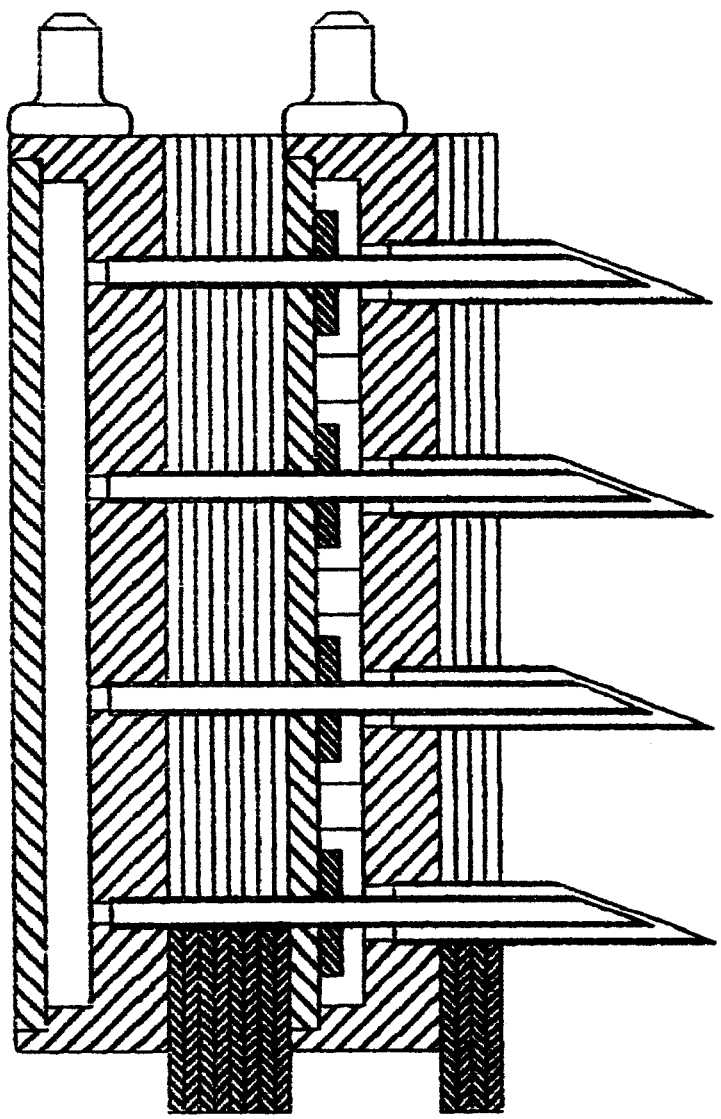

FIGS. 12A–12C illustrate a stationary large area array of needles, which can comprise multiple rows of needles, illustrating a simple design wherein line L1 provides suction for fluids from the area, and line L3 is configured to provide medicinal fluids including coagulants, as earlier discussed, through the needles. The needles may be surrounded by caissons emanating from the base which would receive suction via line L1 for removing blood and medicinal fluids from the area.

In use, the unit would be placed against the skin, such that the caissons enveloping the needles penetrate the skin, the medicinal fluids would be dispensed through the needle, suction from line L1 would direct blood from the area, the needles then lifted while allowing the caissons to continue to collect the fluid from the area. This design is anticipated to exert a trauma to the area, so it would be anticipated for use in emergency, high trauma situations, such as the loss of a limb.

Figure 13A:
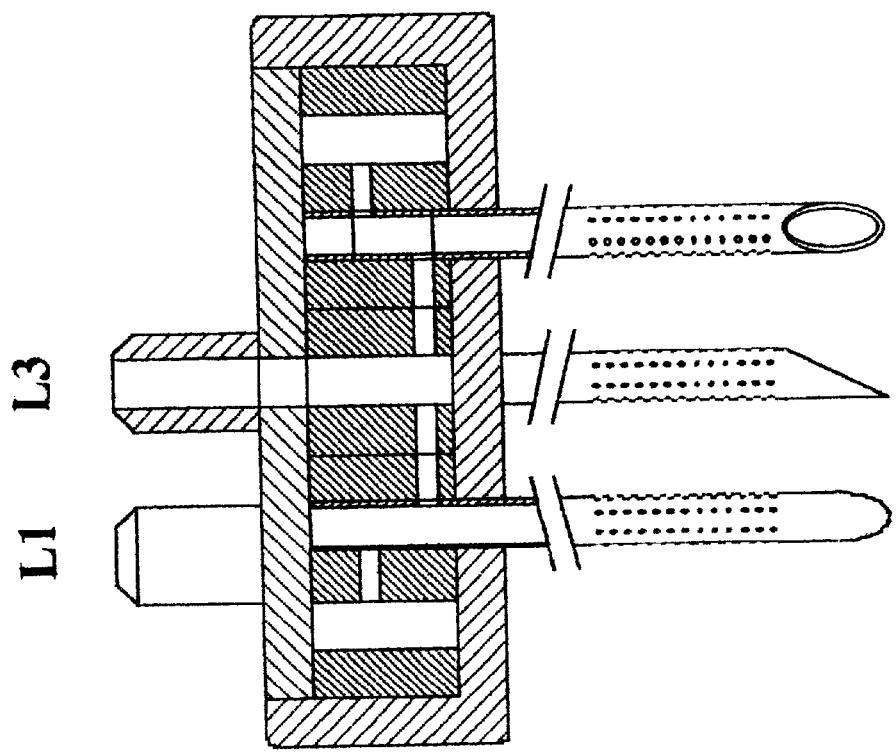
FIG. 13A provides a side, partially cut-away, partially cross-sectional views of a sixth, deep extraction alternative embodiment of the AHM of FIGS. 1A and 1B, illustrating the needle component, extraction base, and associated conduits.
Figure 14A:
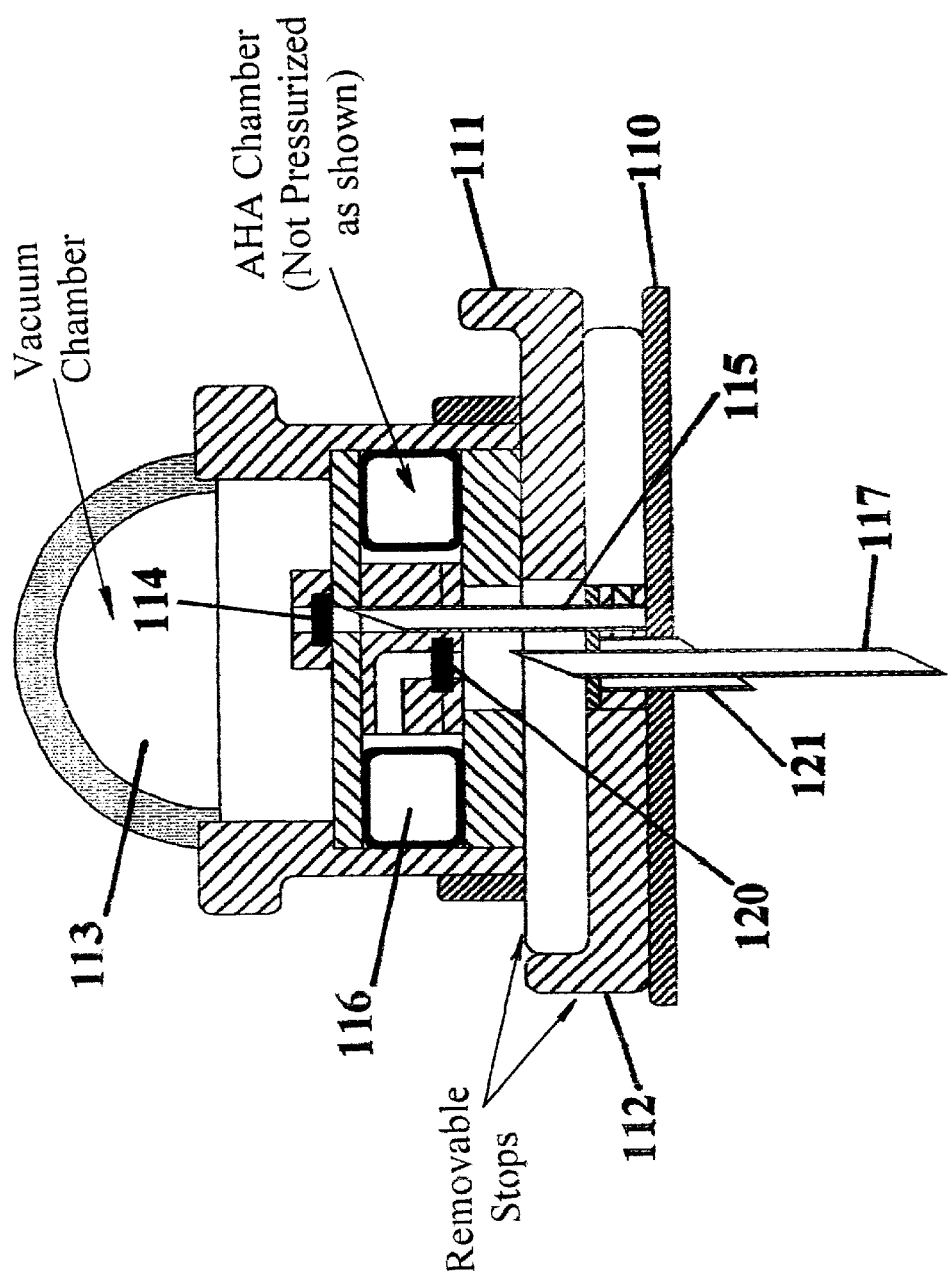
Figure 14B:
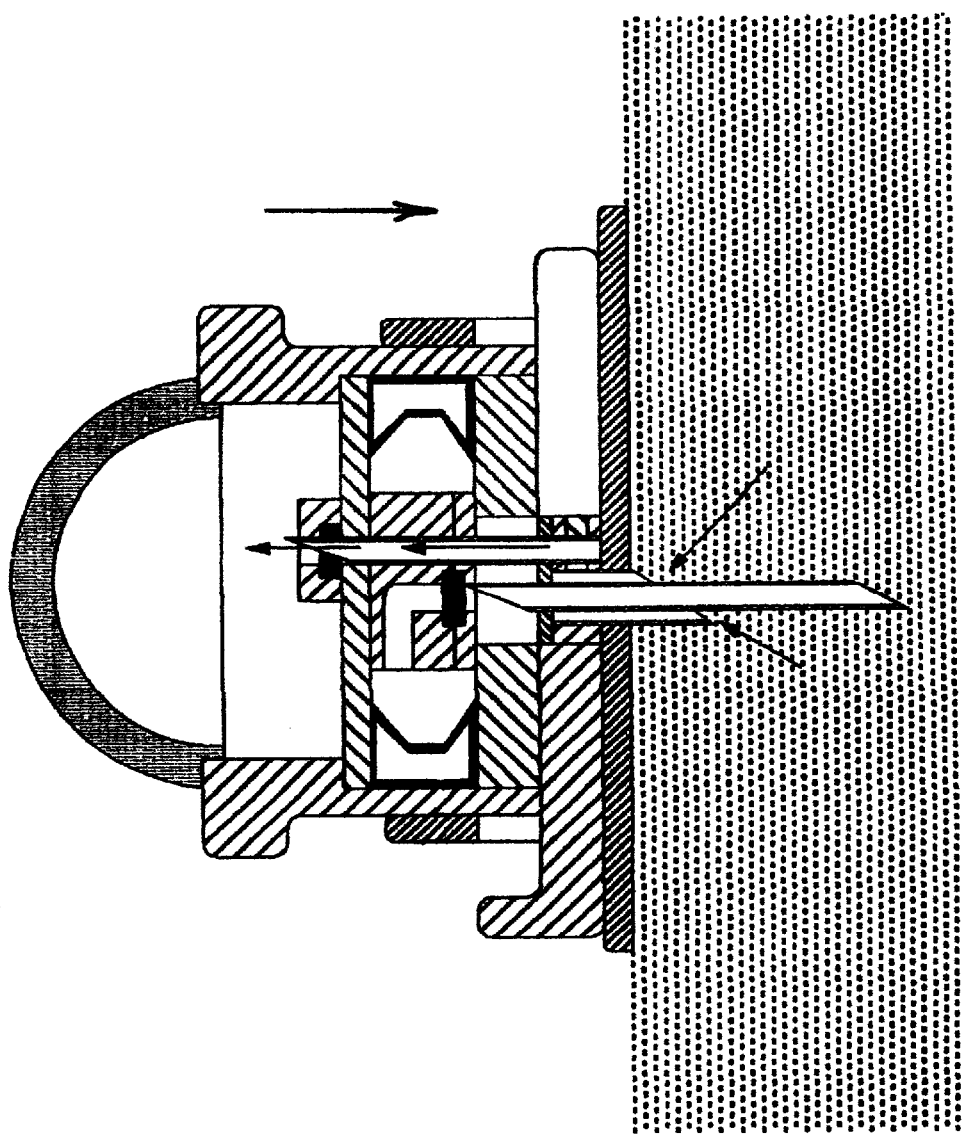
Figure 14D:
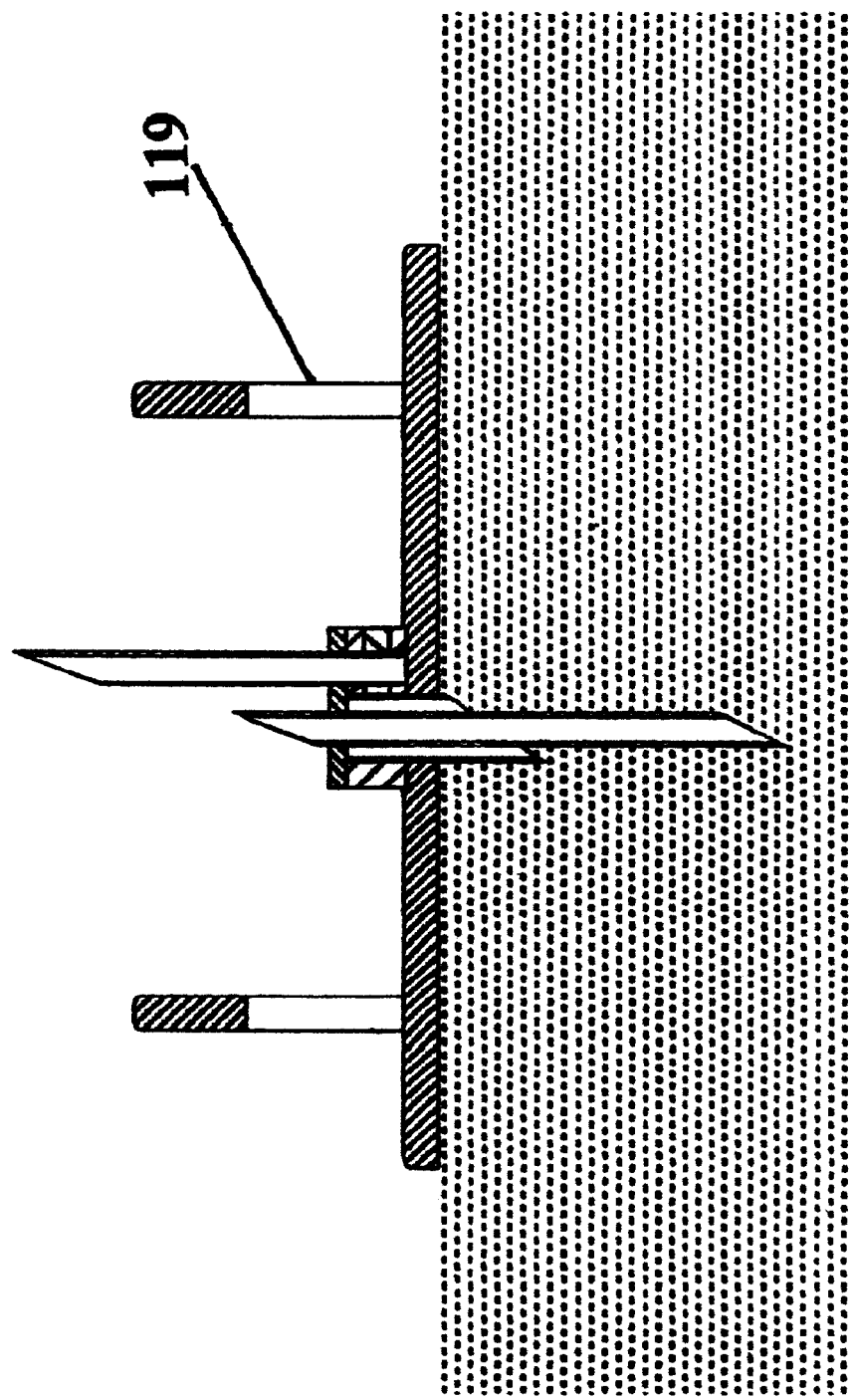
FIG. 14D provides a side, cross-sectional view of the base of the device of FIG. 14A with the main needle implanted into the tissue of an exemplary patient, the base ready for engagement with another extraction unit of FIG. 14A.

FIGS. 13A and 13B illustrate still another embodiment of the present invention, this one designed for deep extraction of fluid from tissue, incorporating a base designed to house the deep extraction needles. The needles, although pointed and designed for piercing the skin, are blocked at the tip, instead including a plurality of orifices 104 situated along the sidewalls of the needle in the vicinity of the needle point. The needle has situated therein a baffle 105 shown in the shape of a helix in order to divide the needle into two internal compartments; one compartment for providing medicinal fluids as earlier discussed, including coagulants, the other for collecting blood. As shown, the base of the unit includes passages communicating with each of the lines L1, L3, providing suction and medicinal fluids, respectively, each accessing a divided area of the needle. Thus, the orifices 104 formed along the sidewall of the needles include those which emit medicinal fluids, and those which provide suction for fluids including blood. The helix design balances the two actions evenly along the length of the needle.

The deep extraction needle is a modified standard hypodermic needle with the side holes cut using and excimer laser. This process is very common in the MEMS field and is available through Potomac Photonics of Lanham, Md. The needle divider is simply a twisted strip of thin stainless steel.

The last alternative embodiment of the present invention varies somewhat from the above designs as it works as a stand alone unit, without the necessity of a control box, and associated hoses, vacuum pumps, etc. As shown in FIGS. 14A–D, the independent, single needle stationary design is intended to emergency use in the field, including a vacuum chamber 113 configured to hold a vacuum till actuated, a suction conduit having a seal 120 communicating with the vacuum chamber, configured to be initiated via downward pressure upon the device, driving the needle through the seal.

In use, the base of the unit is pressed upon the tissue of the patient, such that a needle 117 and enveloping caisson 121 is pressed into the tissue of the patient, causing blood to flow into the base. Next, the first tab, 111 is removed and the unit pressed downward, forcing the first needle 115 through seal 114 opening vacuum chamber and urging blood from the tissue through needle 115 and into the chamber. The chamber is shown with a domed top, which may be transparent so that the collection of blood may be observed. After an interval of time, the second tab 112 may be removed and force again applied downwardly upon the top of the unit, forcing needle 117 through seal 120, opening the medicinal chamber, wherein medicine is urged to flow through the needle and into the tissue via pressure differential. Upon observed filling of the vacuum chamber, the operator may choose to remove the upper portion of the unit, leaving the base 119 upon the patient, and apply an new upper unit to the area to continue the treatment.

The invention embodiments herein described are done so in detail for exemplary purposes only, and may be subject to many different variations in design, structure, application and operation methodology. Thus, the detailed disclosures therein should be interpreted in an illustrative, exemplary manner, and not in a limited sense.

Further, while pneumatic means is illustrated for the various embodiments of the AHM's of the present invention, it is noted that other drive means are available and easily adapted to provide penetration means for penetrating the tissue, incisor means for incising the tissue and other means for performing operational characteristics of the invention, including for example:

Alternatives to the rocking jaw plates illustrated above could include, punches, pivoting rockers, sliders, a shaft driven apparatus including a rotary jaw, slider, tension or torsion rocker, a cable drive apparatus including a flex rocker, circular jaw, punch, rocker jaw, rotary jaw, or a motor drive, including a miniature or microminiature motor driving a circular jaw, rocker jaw, rotary jaw, slider, flex rocker, or the like.

What is claimed is:

1. A mechanical apparatus for stimulating blood circulation in tissue in a patient, comprising:

a device having a housing having a base having formed therein an extraction chamber having a periphery, a blade having a cutting edge associated with said extraction chamber, said blade configured to move relative to said base so as to penetrate the tissue so as to facilitate the discharge of blood from the tissue;

said periphery of said extraction chamber configured to form a seal with the tissue of the patient about said blade when said blade is applied to the patient, said extraction chamber further comprising suction means for providing suction within said extraction chamber to collect the blood discharged from the tissue of the patient.

2. The apparatus of claim 1, wherein said suction means further comprising sealing means for sealingly engaging a portion of tissue of said patient to said extraction chamber in the vicinity of said impaired tissue.

3. The apparatus of claim 2, wherein said sealing means comprises a lip situated about said periphery of said extraction chamber, said lip configured to contact and sealingly engage tissue with the initiation of said suction means.

4. The apparatus of claim 2, wherein there is further provided medication dispensing means configured to dispense medication upon tissue in the vicinity of said extraction chamber.

5. The apparatus of claim 4, wherein said medication is selected from a group of medication including antihistamine, anticoagulant, anesthetic, or antibiotic.

6. The apparatus of claim 5, wherein there is further provided a diaphragm situated within said extraction chamber, said diaphragm forming a wall of said extraction chamber.

7. The apparatus of claim 6, wherein said diaphragm is comprised of flexible, somewhat elastic material.

8. The apparatus of claim 7, wherein said blade is mounted to said diaphragm.

9. The apparatus of claim 8, wherein said apparatus further comprises blade pivot means for pivoting said edge of said blade.

10. The apparatus of claim 9, wherein said blade pivot means is initiated by a piston, said piston motivated by fluid pressure provided by a fluid pressure source.

11. The apparatus of claim 10, wherein said blade has a cutting edge configured for cutting tissue.

12. The apparatus of claim 11, wherein said cutting edge is serrated.

13. The apparatus of claim 5, wherein there is further provided a beam configured of flexible material, said beam having first and second end, said first end communicating with said housing, said second end situated within said extraction chamber.

14. The apparatus of claim 13, wherein said blade is mounted to said second end of said beam in a generally lateral fashion.

15. The apparatus of claim 14, wherein said apparatus further comprises blade pivot means for selectively pivoting said edge of said blade.

16. The apparatus of claim 15, wherein said blade pivot means is initiated by a piston, said piston motivated by fluid pressure provided by a fluid pressure source.

17. The apparatus of claim 16, wherein said piston motivation is communicated to said second end of said beam, causing said beam to flex, thereby rocking said blade supported by said beam.

18. The apparatus of claim 1, wherein there is further provided reciprocating means to reciprocate said blade relative to said base.

19. The apparatus of claim 1, wherein there is further provided medication dispensing means configured to dispense medication upon tissue in the vicinity of said extraction chamber.

20. The apparatus of claim 19, wherein said medication is selected from a group of medication including antihistamine, anticoagulant, anesthetic, or antibiotic.

21. The apparatus of claim 1, wherein said blade is pivotally affixed to said device.

22. The apparatus of claim 21, wherein said apparatus further comprises blade pivot means to selectively pivot said edge of said blade.

23. The apparatus of claim 22, wherein said blade pivot means is initiated by a piston, said piston motivated by fluid pressure provided by a fluid pressure source.

24. The apparatus of claim 1, wherein said periphery of said extraction chamber measures about 1 centimeter.

25. An apparatus for treatment of venous insufficiency in impaired tissue in a patient, comprising:
  a device having a housing having a base having formed therein an extraction chamber having a periphery,
  a blade having a cutting edge associated with said base, said blade configured to move relative to said base so as to penetrate tissue in the vicinity of said extraction chamber, providing a penetration area
  said periphery of said extraction chamber configured to form a seal with the tissue about said penetration area, said extraction chamber further comprising suction means for providing suction within said extraction chamber, so as to urge fluid from said penetration area.

26. The device of claim 25, wherein said blade is configured to selectively communicate with said collection means to pierce said seal sealing said collection conduit.

27. The method of stimulating circulation in tissue, comprising the steps of:
  a) placing a device having an extraction chamber in the vicinity of the tissue;
  b) positioning a penetration member against the tissue in the vicinity of said extraction chamber;
  c) reciprocating said penetration member, so as to form an incision in said tissue by way of said reciprocating motion;
  d) forming a seal with the tissue about the incision with said extraction chamber, and initiating a suction in the extraction chamber, so as to draw blood from said incision;
  e) suctioning a desired amount of blood from the patient so as to stimulate circulation; and
  f) removing the device.

28. The method of claim 27, wherein in after step "a." there is further provided the step "a1." of dispensing to the impaired tissue an anticoagulant and anesthetic.

29. The method of claim 28, wherein the step "e" there is further provided the step "e1," of relieving the suction.

30. The method of claim 28, wherein said penetration member comprises a plurality of needles.

31. An apparatus for treatment of tissue in a patient, comprising:
  a device having a housing having a base having formed therein an extraction chamber having a periphery,
  a blade emanating from said base, said blade having a cutting edge configured to move relative to said base in such a manner as to cut and penetrate tissue situated in the vicinity of said extraction chamber, so as to form an incision;
  said periphery of said extraction chamber configured to engage the tissue about said incision so as to form a seal with said tissue, said extraction chamber further comprising suction means for providing suction within said extraction chamber so as to form a pressure differential in said extraction chamber to urge fluid from said incision.

* * * * *